United States Patent
Radojicic

(10) Patent No.: US 8,764,697 B2
(45) Date of Patent: Jul. 1, 2014

(54) SYSTEMS AND METHODS FOR AN ADVANCED MEDICAL DEVICE

(75) Inventor: Milan Radojicic, Los Gatos, CA (US)

(73) Assignee: Agathos Holdings LLC, Newark, DE (US)

( * ) Notice: Subject to any disclaimer, the term of this patent is extended or adjusted under 35 U.S.C. 154(b) by 0 days.

(21) Appl. No.: 13/332,349

(22) Filed: Dec. 20, 2011

(65) Prior Publication Data
US 2012/0095383 A1 Apr. 19, 2012

Related U.S. Application Data

(63) Continuation-in-part of application No. 11/669,958, filed on Feb. 1, 2007, now Pat. No. 8,096,967.

(60) Provisional application No. 60/766,624, filed on Feb. 1, 2006.

(51) Int. Cl.
*A61M 5/00* (2006.01)

(52) U.S. Cl.
USPC .................................................. 604/8

(58) Field of Classification Search
USPC ............... 604/6.16, 7–10, 266, 891.1; 424/422–426, 93.7, 484; 623/1.4, 1.42, 623/1.43, 1.46, 1.49, 1.16, 1.36, 9
See application file for complete search history.

(56) References Cited

U.S. PATENT DOCUMENTS

| | | | |
|---|---|---|---|
| 3,829,903 A | 8/1974 | Stati et al. | |
| 5,686,289 A | 11/1997 | Humes et al. | |
| 6,348,042 B1 | 2/2002 | Warren, Jr. | |
| 6,579,313 B2 | 6/2003 | Dzau et al. | |
| 7,049,057 B2 | 5/2006 | Atala et al. | |
| 8,096,967 B2 * | 1/2012 | Radojicic | 604/9 |
| 2006/0069425 A1 | 3/2006 | Hillis et al. | |
| 2007/0082393 A1 | 4/2007 | Lodhi et al. | |
| 2007/0179427 A1 | 8/2007 | Radojicic | |
| 2009/0227025 A1 | 9/2009 | Nichols et al. | |
| 2011/0004304 A1 | 1/2011 | Tao et al. | |
| 2011/0060265 A1 | 3/2011 | Dragoon et al. | |

OTHER PUBLICATIONS

Baizabal, J.-M., et al., Neural Stem Cells in Development and Regenerative Medicine, Arch. Med. Res 34, 2003, pp. 572-588.
Cornford, E., et al., Localization of Brain Endothelial Luminal and Abluminal Transporters with Immunogold Electron Microscopy, NeuroRx: The Journal of the American Society for Experimental NeuroTherapeutics, vol. 2, Jan. 2005, pp. 27-43.

(Continued)

*Primary Examiner* — Philip R Wiest
(74) *Attorney, Agent, or Firm* — Kang S. Lim

(57) ABSTRACT

The present invention relates to a biologically active medical device, which includes a matrix seeded with progenitor cells, and then covered by ciliated tissue. The matrix is capable of enabling cellular migration. The ciliated tissue is ependymal cells that express at least one of tight junctional complexes, zonula adherens, and gap junctions. The progenitor cells include subependymal progenitor cells. In some cases the progenitor cells include stem cells, and the ciliated tissue includes at least one of Choroid cells, tanacytes, and circumventricular organs. In some embodiments, the medical device is oriented into a tubular structure in order to form a cerebrospinal shunt. Additional cells and structures may be imbedded within the matrix, such as glia, endothelial cells, stem cells, and blood vessels. The medical device may also be incorporated into a bioreactor including a flexible inner tube defining an anthropomorphically shaped lumen.

11 Claims, 22 Drawing Sheets

(56) References Cited

OTHER PUBLICATIONS

Duval, J.-L., et al., Use of the organotypic culture method to investigate drug-loaded CSF shunt, Journal of Controlled Release 116, 2006, pp. e50-e53.

Gabrion, J.B., et al., Ependymal and Choroidal Cells in Culture: Characterization and Functional Differentiation, Microscopy Research and Technique 41, 1998, pp. 124-157.

ISA/KR, PCT International Search Report and Written Opinion, Application No. PCT/US2012/070415, dated Apr. 10, 2013, 11 pages.

Koizumi, J., et al. Changes of Gap and Tight Junctions during Differentiation of Human Nasal Epithelial Cells Using Primary Human Nasal Epithelial Cells and Primary Human Nasal Fibroblast Cells in a Noncontact Coculture System, J Membrane Biol 218, 2007, pp. 1-7.

Radojicic, Milan, The Bioshunt, Retrieved Mar. 28, 2007 from http://www.deomedicus.com/education/the-bioshunt, html., Feb. 1, 2007.

Seminatore, C., et al., The Postischemic Environment Differentially Impacts Teratoma or Tumor Formation After Transplantation of Human Embryonic Stem Cell-Derived Neural Progenitors, Stroke 41, 2010, pp. 153-159.

Ziegelaar et al. "The characterization of human respiratory epithelial cells cultured on resorbable scaffolds: first steps towards a tissue engineered tracheal replacement", Biomaterials, vol. 23, 2002, pp. 1425-1438.

\* cited by examiner

SYSTEMS AND METHODS FOR AN ADVANCED MEDICAL DEVICE

CROSS REFERENCE TO RELATED APPLICATION

This application is a continuation in part and claims priority to U.S. application Ser. No. 11/669,958 filed on Feb. 1, 2007, entitled "Tissue Engineered Cerebrospinal Fluid Shunt", recently allowed, which claims priority to U.S. Provisional application Ser. No. 60/766,624 filed on Feb. 2, 2006, both applications are hereby fully incorporated by reference.

BACKGROUND

The present invention relates to systems and methods for advanced medical devices, and in particular related to advanced cerebrospinal shunts, applications of shunt based therapies, and unique bioreactor designs that may mimic cerebrospinal environments with unprecedented accuracy. Such systems and methods provide for therapies that can treat disease states that were previously considered untreatable, increase the success of current cerebrospinal shunt treatments, and advance research into cerebrospinal pathology and physiology.

Shunts have longstanding been utilized by the medical community to move fluid from one part of the body to another. For example in ventriculoperitoneal shunting, one or more catheters are placed unto the vertical of a patient's brain, and extend down to the abdominal or chest cavity (often into the peritoneal cavity). A pressure valve or fluid pump may attach to the catheter(s) in order to allow fluids to exit the brain if the pressure rises above desired levels. Additionally, the valve prevents backflow of blood or other fluids into the brain. There are many valve designs that may accomplish various flow characteristics.

Typically shunt catheters are made of biocompatible materials, and are often selected based upon their final usage. Common shunt catheter materials include silicones, polyvinyl chloride (PVC), and latex rubber. Unfortunately, shunt failures may result from blockage of the proximal and/or distal catheters due to tissue ingrowth, cellular debris and clot, as well as shunt infection. Valve malfunctions are also possible. These frequent failures result in undue patient morbidity and mortality.

In response to these complications frequently associated with traditional shunts, additional and more exotic shunt materials have been experimented with. These newer shunt materials have been designed to include bioactive compounds, such as antimicrobial compounds, anticoagulation, and protein degradation compounds. Some shunts have also been proposed that include bioactivity, such as seeded shunts and enzymatically active shunts.

These newer shunt designs have come about for a variety of reasons, primarily related to buildup of protein, cellular debris, minerals, or other potential occlusions that negatively impact the flow characteristics of the shunt. While these advancements have been met with some degree of success, there is always a need for improved shunt designs that will provide long-term, cost effective, favorable flow characteristics in increasingly smaller luminal profiles.

Additionally, new interest has developed in utilizing shunts as not only a fluid pathway, but also as a broader therapeutic tool. This may include adding in properties that extend beyond mere fluid flow, but also increase patient health.

One area that has received particular interest is in cerebrospinal shunts. The diversion of cerebrospinal fluid from one location to another where it may be disposed is a well-known clinical strategy for a number of brain and spinal disorders, and is one of the most common neurosurgical procedures. Improving cerebrospinal shunt designs would have a marked impact upon a large number of patient's requiring this kind of procedure.

The cerebrospinal fluid flow has two components. A bulk flow from the production and absorption of cerebrospinal fluid and a pulsatile/oscillatory flow from influence of the cardiac cycle on the bulk flow. Also, there are respiratory and body positional influences on the cerebrospinal fluid flow.

With every heartbeat, a volume of blood enters the brain via the carotid and vertebral arteries, causing the brain to expand in the skull, which is a fixed container. This forces CSF out of the cranial cavity into the spinal subarachnoid reservoir, until diastole when the CSF is reversed. The CSF dampens the oscillations of the brain preventing injury. But in some CNS injury and disease the CSF production is diminished, so the pulse pressure (difference between systolic and diastolic pressures) can itself become an injurious process, the so-called pulse pressure encephalopathy.

It stands to reason that the long acting pressure changes along with ventricular lining and spinal central canal can injure the endothelium, which is comprised on ependymal cell and subependymal stem cells. Ependymal cells produce and process the CSF. Specialized ependymal cells in association with a capillary network are known as the choroid plexus. Damage to the ependyma and choroid can influence CSF production and reduce the dampening effect of cardiac pulsations, as well the clearance of toxic ions, proteins and metabolites.

Means for addressing the problems complacent with cerebrospinal shunts, replacement of CSF, and repair of cellular members that are involved in regulating the CSF environment could have significant clinical and research value.

It is therefore apparent that an urgent need exists for an improved cerebrospinal medical device that enables more efficient and longer lasting fluid flow properties in a cerebrospinal shunt, improved therapies, and enhanced research into cerebrospinal pathologies and treatments.

SUMMARY

To achieve the foregoing and in accordance with the present invention, systems and methods for an improved medical device is presented. Such systems and methods enable enhanced therapies, diagnostics, and research opportunities.

In some embodiments, a biologically active medical device is provided which has a luminal surface and an abluminal surface. The medical device includes a matrix seeded with progenitor cells, and then covered by ciliated tissue. The matrix is capable of enabling cellular migration. The ciliated tissue is ependymal cells that express at least one of tight junctional complexes, zonula adherens, and gap junctions. The progenitor cells include subependymal progenitor cells. In some cases the progenitor cells include stem cells, and the ciliated tissue includes at least one of Choroid cells, tanacytes, and circumventricular organs. In some embodiments, the medical device is oriented into a tubular structure in order to form a cerebrospinal shunt.

Additional cells and structures may be imbedded within the matrix, such as glia, endothelial cells, stem cells, and blood vessels. The matrix may be made of silicones, polyurethane, polyethylene, polypropylene, polyvinyl chloride, agarose gel, collagen, elastin, capillary networks include fibronectin and endothelial cells.

In some embodiments, the medical device as may also includes a microfluidic circuit coupled to the abluminal surface of the matrix. The medical device may also be incorporated into an anthropomorphic bioreactor. The anthropomorphic bioreactor includes a ridged outer surface for housing internal components, a flexible inner tube defining an anthropomorphically shaped lumen. The bioreactor also includes a series of ports that enable bulk flow control over fluid inside the lumen, as well as sensor access. An oscillating pump may also provide pulsatile flow of the fluid.

Often, the fluid within the bioreactor is cerebrospinal fluid and/or synthetic cerebrospinal fluid. In some embodiments, the anthropomorphic bioreactor produces and processes the cerebrospinal fluid, including filtering the cerebrospinal fluid of a patient and mimicking disease states for research purposes.

In some embodiments, such a bioreactor can be used to select for robust cells. This is accomplished by seeding the bioreactor with target cells, applying shear stresses to the target cells in a manner consistent with physiological conditions, maturing the cells, and collecting the cells. Only robust cells will survive, and as such the collected cells are more capable of surviving harsher conditions. In some cases the stresses applied include metabolic perturbations, temperature stresses, chemical stresses, osmolality stresses, radiation stresses, acoustic stresses, and electromagnetic stresses.

Note that the various features of the present invention described above may be practiced alone or in combination. These and other features of the present invention will be described in more detail below in the detailed description of the invention and in conjunction with the following figures.

BRIEF DESCRIPTION OF THE DRAWINGS

In order that the present invention may be more clearly ascertained, some embodiments will now be described, by way of example, with reference to the accompanying drawings, in which.

DETAILED DESCRIPTION

Figure 1:
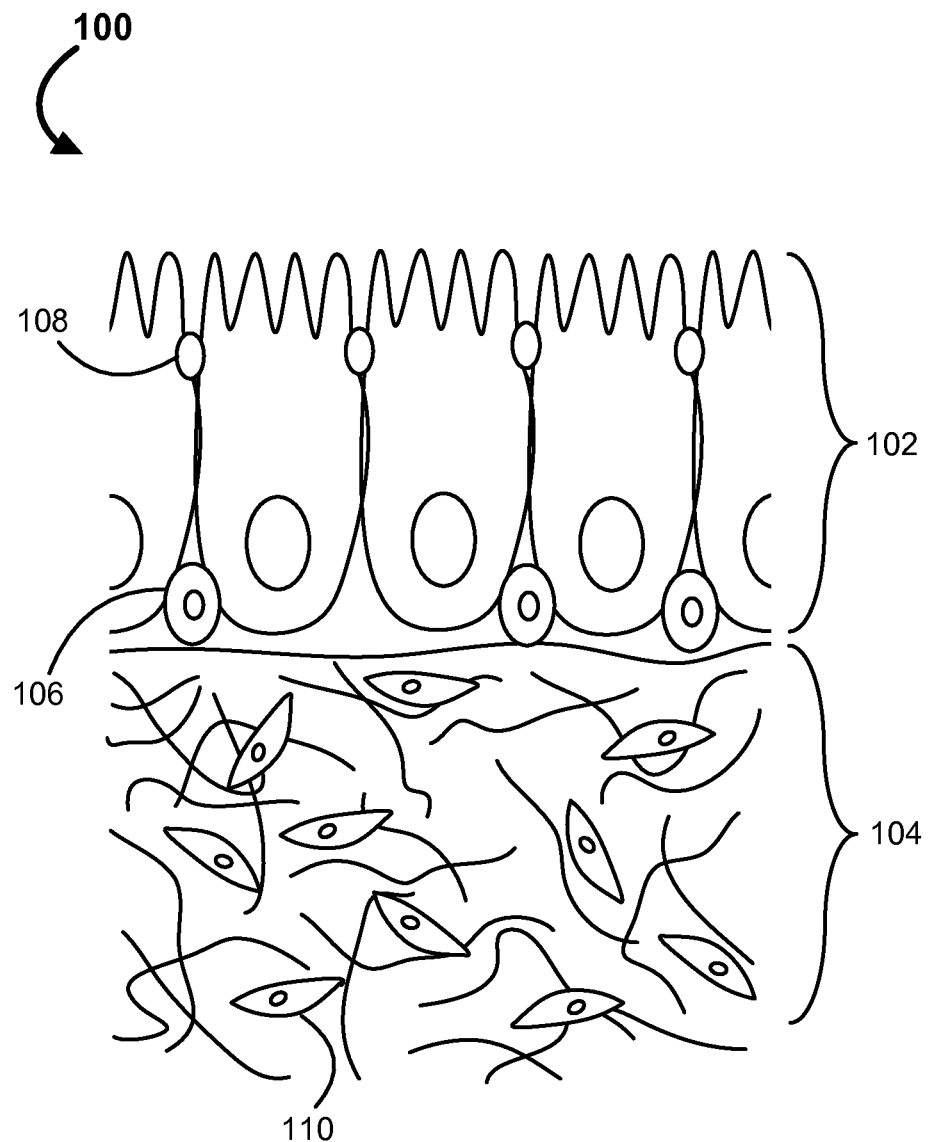
FIG. 1 is an example cross sectional illustration of an improved medical device surface, in accordance with some embodiments.

The present invention will now be described in detail with reference to several embodiments thereof as illustrated in the accompanying drawings. In the following description, numerous specific details are set forth in order to provide a thorough understanding of embodiments of the present invention. It will be apparent, however, to one skilled in the art, that embodiments may be practiced without some or all of these specific details. In other instances, well known process steps and/or structures have not been described in detail in order to not unnecessarily obscure the present invention. The features and advantages of embodiments may be better understood with reference to the drawings and discussions that follow.

The present invention relates to a novel and improved medical device that has application in cerebral spinal shunt design, bioreactor design, and unique therapies. Central to these systems and methods is a unique three dimensional matrix that includes biological elements, and a luminal surface of ciliated tissue. Such a medical device enables improved flow characteristics of cerebral spinal fluid (CSF) though shunt material, prevention of occlusion due to protein buildup or tissue ingrowth, release of biological agents and CSF production, and more accurate modeling of the cerebral spinal fluid pathways.

In some embodiments, it is an object to provide new and additional auxiliary means for intraluminal fluid propulsion, namely through the introduction of ciliated cellular elements. It is also an object to regulate the tonicity and translocation of intraluminal fluid by inherent cellular mechanisms. Furthermore, it is an object to prevent blockages of the fluid pathway through inherent enzymatic processes of the intraluminal matrix cells. Finally, recent attention has turned to the role of the cerebrospinal fluid flow and stem cell behavior. It is an object of this invention to seed stem/progenitor cells along the intraluminal matrix to provide for local and remote brain and spinal cord repair. This further results in a new system with improved properties over prior systems. Other objectives will be readily apparent based on the following detailed description.

Note that while much of the discussion contained herein relates to a medical device that includes a cerebrospinal shunt like orientation (that is a tubular structure including an interior lumen that is in contact with the CSF), the medical device is capable of existing in a variety of orientations, as is desired for any particular application. For example, for a physiological mimicry bioreactor, complex three dimensional shapes may be desired rather than a simple tubular structure. Likewise, it may be desirable to include layers of ciliated membranes, or other medical device orientations. As such, disclosures directed to a shunt, for example, should be understood to apply not only to a tubular structure, but extends to all conceivable medical device orientations and geometries. In the same theme, the term "lumen" is intended to refer to the space where the CSF resides, regardless of the cavity geometry.

The following description of some embodiments will be provided in relation to numerous subsections. The use of subsections, with headings, is intended to provide greater clarity and structure to the present invention. In no way are the subsections intended to limit or constrain the disclosure contained therein. Thus, disclosures in any one section are intended to apply to all other sections, as is applicable.

I. Biologically Active Medical Device

A. Structure

To facilitate the discussion, some embodiments of the medical device relate to a biocompatible shunt for the diversion of cerebrospinal fluid, in which the luminal surface is seeded with at least one population of cells. The purpose of the disclosed medical device is to more accurately mimic natural cerebrospinal conditions and structures in order to more efficiently control fluid characteristics, provide therapies, and model natural cerebrospinal conditions. FIG. 1 is an example cross sectional illustration of an structure that would be usable for such an improved medical device surface, shown generally at 100.

In this example illustration, the surface that is in contact with the cerebrospinal fluid (the lumen in a shunt) is illustrated on the top, whereas the surface that contacts tissue (exterior surface of the shunt) is illustrates on the bottom. In many embodiments, the luminal facing layer of cells 102 may be selected based upon some characteristics which make them suitable for this application. These characteristics include: 1) apical cilia whose rhythmic beating promotes cerebrospinal fluid flow across the surface and prevents obstruction of fluid flow by tissue, clot and/or debris; 2) tight junctions that prevent translocation of intraluminal fluid; 3) cellular mechanisms to regulate the tonicity of intraluminal fluid through selective ion and protein exchange; and 4) cellular mechanisms for the spontaneous and continuous production, storage and release of enzymes that assist in the degradation of intraluminal tissue, clot and debris thereby maintaining patency of the shunt.

In some embodiments, the outer layer of cells 102 is comprised of a polarized ependymal epithelial phenotype with tight junctional complexes 108 and apical cilia directed toward the lumen of the catheter (or other CSF contacting surface in a non-tubular structure). In some particular embodiments, the layer of cells 102 may be further specialized to include Choroid cells. Choroid cells are highly specialized bundles of ependymal interspersed with blood vessels/capillaries. Choroid cells are also a form of ciliated epithelia, which produce and process the CSF, and therefore have implications for improving long term patient health when included in an implanted medical device, or in a specialized bioreactor device designed for therapeutic purposes. Other particular embodiments may include specialized ependyma, known as tanacytes, that contact neurons and capillary networks and serve neuroendocrine and transport function. Finally, other particular embodiments may mimic the circumventricular organs, which are specialized ependyma in direct contact with the blood and cerebrospinal fluid and regulate body fluid homeostasis.

The tight junctional complexes 108 couple the ependymal cells into a cohesive tissue. In addition to providing an indication of tissue maturity, cellular signaling, and physical durability, such tight junctions are generally impermeable to water, and therefore protect lower layers of the medical device from inadvertent exposure to CSF and the signaling proteins contained therein. In such a way, lower layers of the medical device may incorporate other cell types, including stem and progenitor cells, without concern of inappropriate or premature differentiation. Other specialized cell junctions will be selected in some embodiments, including zonula adherens type junctions, as well as gap junctions, the latter being important for certain cell signaling applications.

Below the ciliated epithelium layer 102 are interspersed subependymal progenitor cells 106, or other stem cells, which may guide local and remote repair of the ciliated epithelium layer 102. Cells have a finite life and most cell populations require regular turnover. The incorporation of a layer of stem/progenitor cells allows for local repair of denuded epithelium, thereby extending the life of the medical device. Additionally, research suggests that such subependymal progenitor cells 106 may have cilia-like projections that extend into the CSF space for cellular signaling purposes. Furthermore, some embodiments may allow for the differentiation, proliferation and migration of glial and neural precursors from the shunt intraluminal matrix into surrounding neural tissue for the purposes of therapeutic cell delivery and wound repair. In some embodiments, these cells are impregnated on a matrix coating the luminal surface of the shunt prior to the application of the ciliated epithelium layer 102.

Below the ciliated epithelium layer 102 is a biocompatible matrix 104 that may include one or more other cells 110 as is desired for any particular application. These other cells may include any of glia, endothelial cells/capillaries/vessels, stem cells, or other desired cell types. In some embodiments, no seeded cells may be included in the matrix 104, and in other embodiments a number of different cells may be included, dependent upon end application and desired properties.

The biocompatible matrix 104 itself may vary in terms of composition, thickness, and manufacturing process depending upon desired characteristics. Measures such as strength, porosity, biocompatibility, rate of degradation, flexibility (or rigidity) and the like may have a significant influence on the matrix. For example, a shunt that is expected to have a large pressure differential may need to be made of a more robust and thicker material, than one that experiences a smaller pressure differential. A greater degree of porosity may promote increased endogenous cellular ingrowth. Some materials may degrade faster than others, which may be desirable of sustained drug release, for example. The matrix may be bioabsorbable, which allows the cells to generate their own extracellular matrix over time.

In many embodiments the medical device needs to be sufficiently flexible to be implanted in the patient, however, in some embodiments a more rigid device may be desired.

Often the matrix 104 is composed of a polymer, such as silicones, polyurethane, poly ethylene, poly propylene, and polyvinyl chloride. Of course alternate matrices may likewise be utilized, such as agarose gel, collagen matrix, elastin matrix, or some combination of the above. Additionally, more exotic materials could also be employed, as is desirable for the specific properties they provide.

In addition to potentially seeding the biocompatible matrix 104 with cells 110, the matrix may be generated to contain, and even release, antimicrobial compounds, growth factors, cellular signaling compounds, and the like in order to further promote medical device operability. For example, the matrix 104, in some embodiments, may include growth factors the promote neurogenesis in order to more rapidly integrate a shunt, for example, into its implanted position. Stem cells are localized in specialized niches that regulate self-renewal and cell-fate. The interaction of cells and matrix involves complex, spatially and temporally coordinated collections of chemokines, cytokines, growth factors, membrane receptors and extracellular matrix molecules, along with the biophysical and biomechanical environment of the niche. The system would allow for therapeutic and research applications that involve coordinated cell-cell interactions, cell-matrix and cell-soluble factors relations, also known as stem cell programming.

Figure 2:
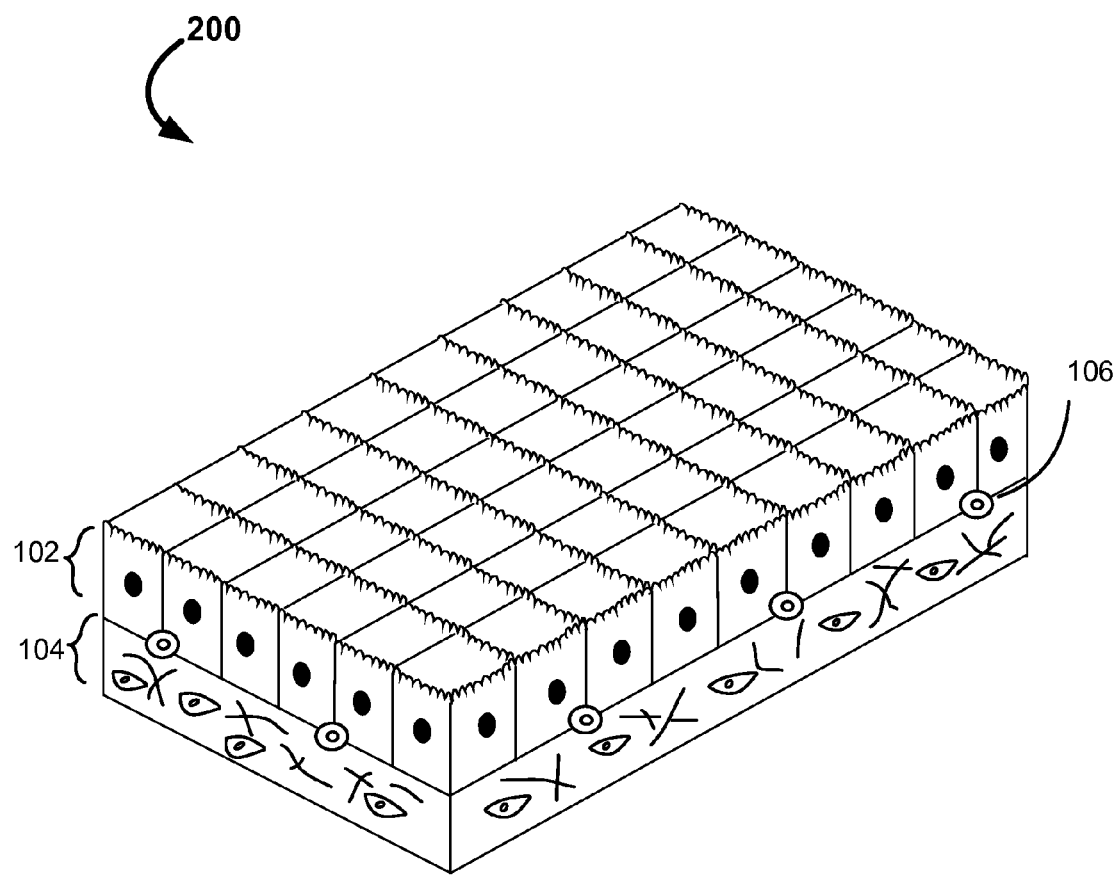
FIG. 2 is an example isometric illustration of an improved medical device surface, in accordance with some embodiments.

FIG. 2 is an example isometric illustration of an improved medical device surface, shown generally at 200. This example illustration merely illustrates that the device may extend as a sheet or membrane. This surface may thus be utilized to form into tubules, or more complex three dimensional (3D) shapes as is desired. In this illustration, the ciliated epithelium layer 102, biocompatible matrix 104, and subpendymal progenitor cells 106 are visible. However, due to scale, other components of the medical device structure are no longer discernible.

Figure 3:
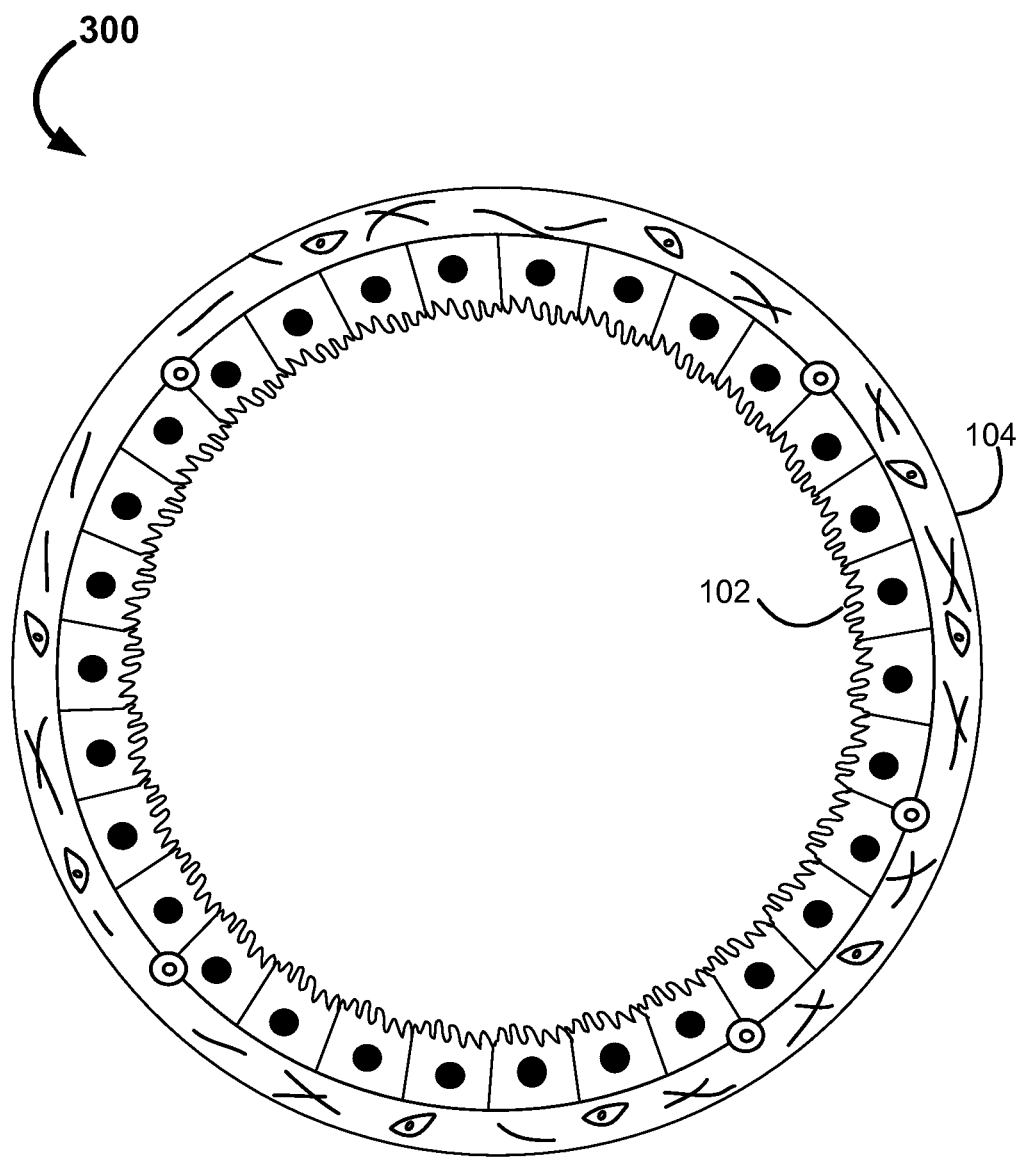
FIG. 3 is an example cross sectional illustration of an improved medical device oriented into a shunt structure, in accordance with some embodiments.

Continuing, FIG. 3 is an example cross sectional illustration of an improved medical device oriented into a shunt structure, shown generally at 300. Here the medical device multi-layered structure has been wrapped into a tubular geometry, as would be found for most shunts. The ciliated epithelium layer 102 faces inward, into the lumen where the cerebrospinal fluid flows. This flow may be according to a pressure gradient, or may be as a result of cilia movement, or both. The biocompatible matrix 104 may face outward, and may contact surrounding tissue. Materials of the matrix 104, growth factors, and/or impregnated cells 110 may increase the rate at which the medical device has endogenous cellular ingrowth.

Figure 4:
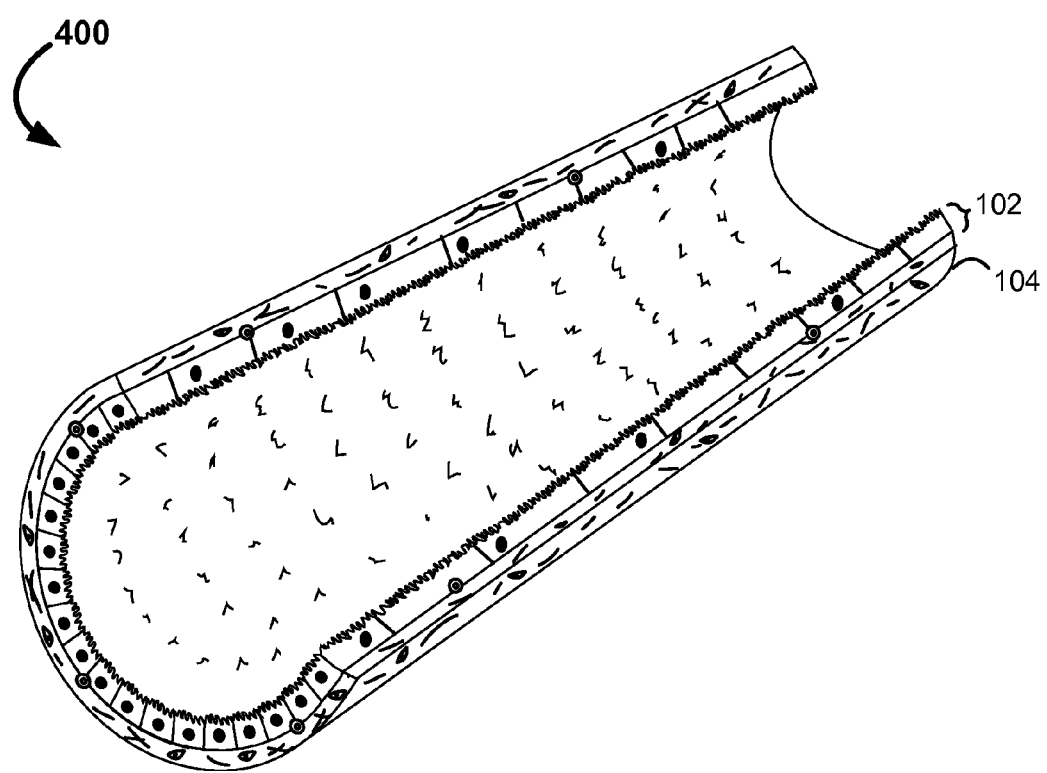
FIG. 4 is an example isometric cutaway illustration of an improved medical device oriented into a shunt structure, in accordance with some embodiments.

FIG. 4 is an example isometric cutaway illustration of an improved medical device oriented into a shunt structure, shown generally at 400. This illustration more clearly shows the tubular structure of this embodiment of the medical device.

B. Pathways and Therapeutics

Figure 5:
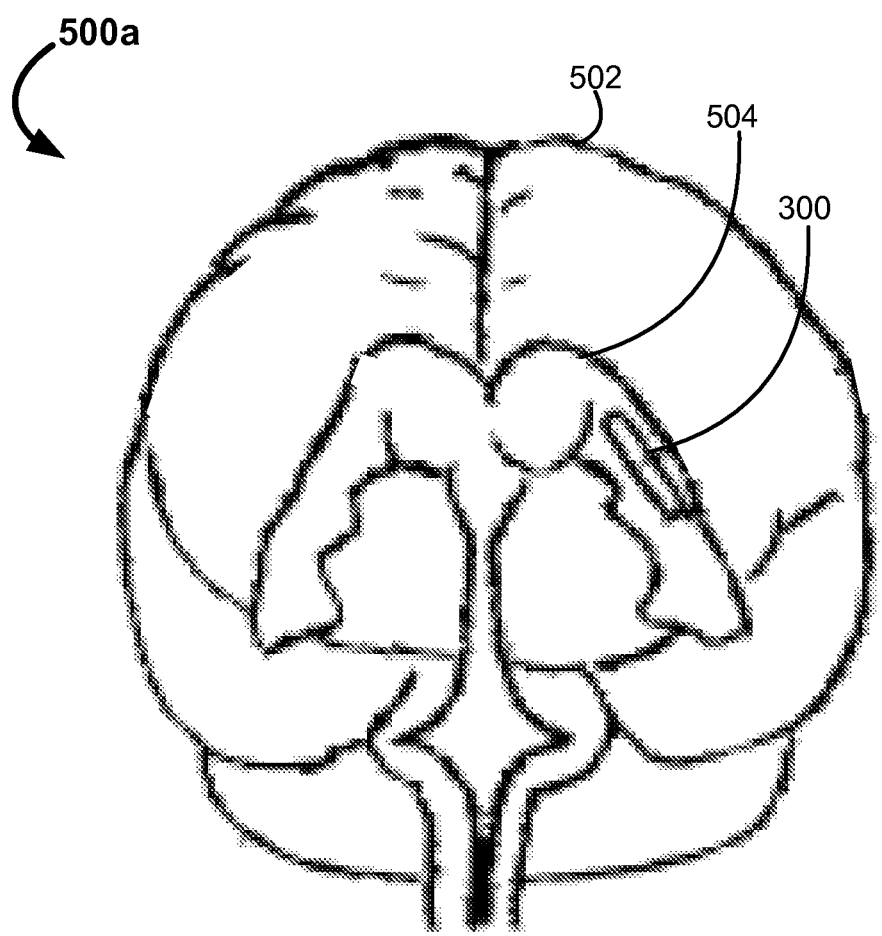
FIGS. 5 and 6 are example illustrations of the improved medical device oriented into a shunt structure being utilized within a patient, in accordance with some embodiments.
Figure 6:
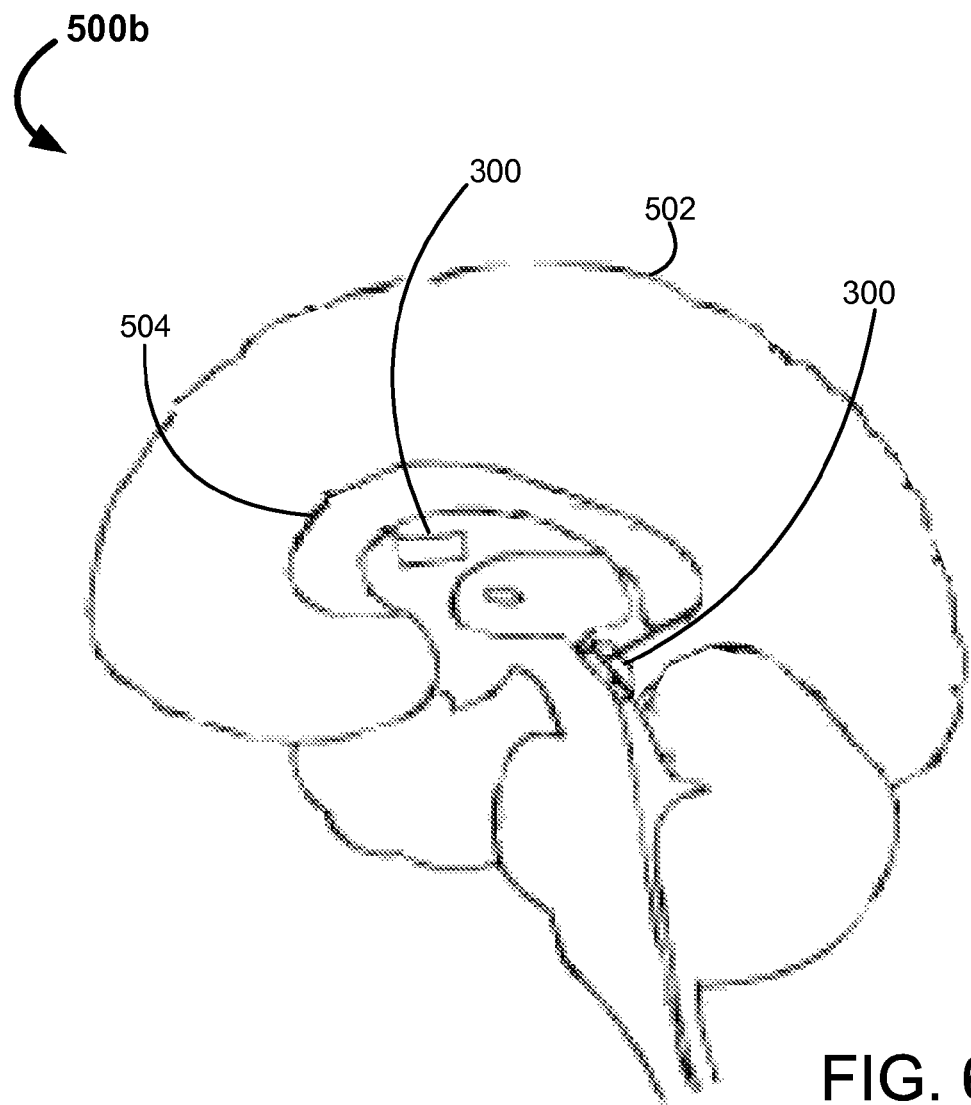

In addition to providing an improvement in design over existing cerebrospinal shunts, the disclosed medical device is capable of being implemented in ways not previously possible using existing shunts. This enables new and advanced therapies, examples of which can be seen in relation to FIGS. 5 and 6, which illustrate the improved medical device oriented into a shunt structure being utilized within a patient's brain, seen generally at 500a and 500b respectively.

In these example illustrations the tubular shunt 300, is seen residing in the ventricle 504 and other cavities of the patient's brain. The cortex tissue 502 is also illustrated for clarification. The placement of the shunts, in these example illustrations, is to address the fact that sometimes entirely new fluid pathways need to be created within the patient.

In some embodiments, the shunt 300 or prosthesis may be of a more complex three dimensional shape inside the ventricular CFS pathway to replace missing or scarred endogenous pathways (or generation of brand new pathways).

Prior shunt designs would be ineffective at this kids of replacement therapy because the luminal surface of these prior shunts is not biologically active in the manner of the presently disclosed medical device. Here a ciliated tissue is disclosed that is able to control tonicity and osmolality, and to some degree, composition of the CSF. Occlusion, and protein buildup are also addressed due to the enzymatic and mechanical properties of the ciliated tissue. Since the tissue is capable of replacement, the disclosed medical device is capable of addressing the needs of the patient for a longer term than traditional shunts are capable of.

C. Methods of Manufacture

Figure 7:
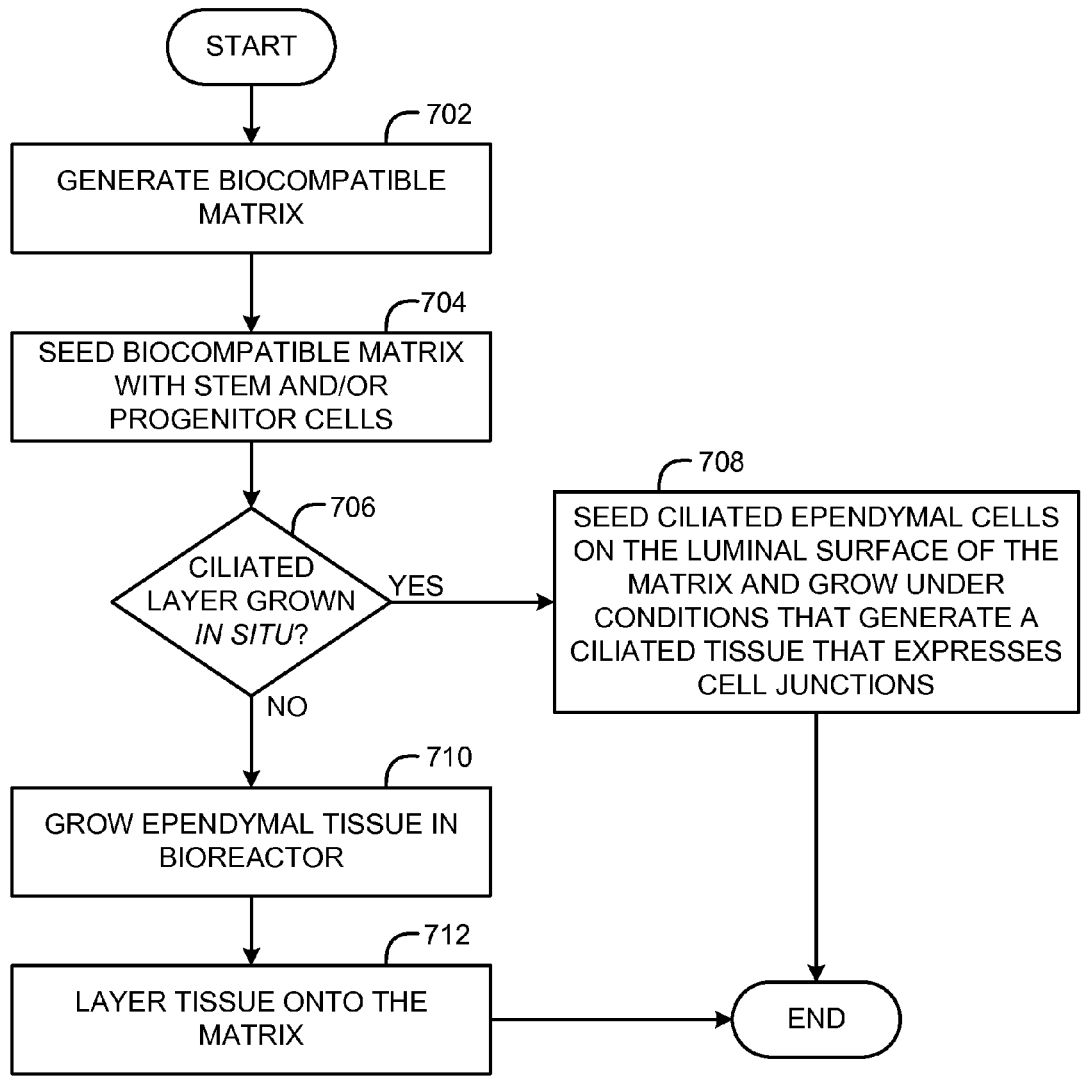
FIG. 7 is an example flow chart for the process of generating an improved medical device, in accordance with some embodiments.

FIG. 7 is an example flow chart for the process of generating an improved medical device. It should be noted that the disclosed means for the generation of such a medical device is for example purposes only, and a number of alternate means for medical device manufacture may likewise be employed.

In this example process the biocompatible matrix 104 is first generated (at 702). The generation of the biocompatible matrix may be generated through known molding techniques for polymer materials, 3D printing, machining, casting or other suitable technique. In some embodiments, the newly generated matrix may be sterilized using an autoclave, chemical means or irradiation.

In some embodiments, the matrix may further be impregnated with one or more cell types. In these embodiments, the cells may be included in the polymer or gel during low temperate molding or casting. In these embodiments, the matrix will be generated in sterilized conditions in order to avoid the requirement of later sterilization which would kill the embedded cells. Alternatively, these cells may be impregnated into the matrix by forcing a solution including the cells across the matrix under pressure. Generally, the solution will pass through the porous matrix and the larger cells will become lodged within the fibers of the matrix.

Next the matrix 104 may be seeded with stem/progenitor cells (at 704). This seeding of the subpendymal progenitor cells 106 may be accomplished via impregnation as described above, or simply by placing a serum including these stem cells in contact with the luminal surface of the matrix and allowing the cells to adhere to the matrix's surface.

Next, a decision is made (at 706) whether the ciliated epithelium layer 102 is to be grown in situ on the matrix, or will be grown separately and applied to the matrix subsequently. If the tissue layer is to be grown in situ the luminal surface may be seeded with progenitor, stem cells, or even further differentiated cells, and these cells may be induced to further divide and differentiate on the surface of the luminal surface of the matrix until a full tissue is formed (at 708). Maturity of the tissue may be measured by the formation of tight junctions, and physical adherence to the matrix.

If the tissue is not grown in situ, the cell culture may be grown in bioreactor (at 710) and transferred to the matrix once the tissue is sufficiently matured (at 712). In some embodiments, the measure of maturity may again be measured by the presence of cell junctions, including zonula adherens, tight junctions or gap junctions. However, in alternate embodiments, the maturity of the tissue may be measured through transcription indicators, as measured using reverse transcription polymerase chain reaction (RT-PCR), specific protein expression, phonotypical indicators (such as cilia shape and/or density), and/or by cellular density. Maturity may also be assessed via trans epithelial electrical resistance or related functional studies.

The tissue may be dislodged from the bioreactor using trypsin solution, or other known laboratory techniques, and the dislodged tissue may be layered onto the matrix, and induced to adhere to the luminal surface of the matrix.

Once the complete medical device has been formed, it may be maintained in a bioreactor, or alternatively treated and cooled to preserve its shelf life. In some embodiments, the medical device may be treated with glycerol or other anti-ice-nucleation agent, and frozen for long term storage. When maintained in a bioreactor, it may be desirable to have a continuous and/or pulsating fluid flow over the luminal surface of the medical device in order to induce the proper shear forces on the ciliated epithelium layer 102. These shear forces have been shown to be important in maintaining proper cellular activity and normal tissue characteristics.

II. Novel Therapies

In addition to being able to perform shunt procedures better than traditional cerebrospinal shunts, be incorporated into a patient's CSF pathway for long term replacement of endogenous tissue, and the generation of new pathways, the presently disclosed medical device also has advantages in novel cellular repair therapies due to its unique biological properties.

Currently stem cell therapies are practiced using needles or catheters that deliver loose cells into the area of the patient that requires repair. Such therapies are still experimental, and aim to replace neurons that have been destroyed due to trauma, or neurodegeneration due to pathology, such as from a stroke or tumor. These loose stem cells often clump together and may block CSF pathways and form micro-cysts. This undesirable clumping may limit the efficiency of traditional stem cell therapy.

Figure 8:
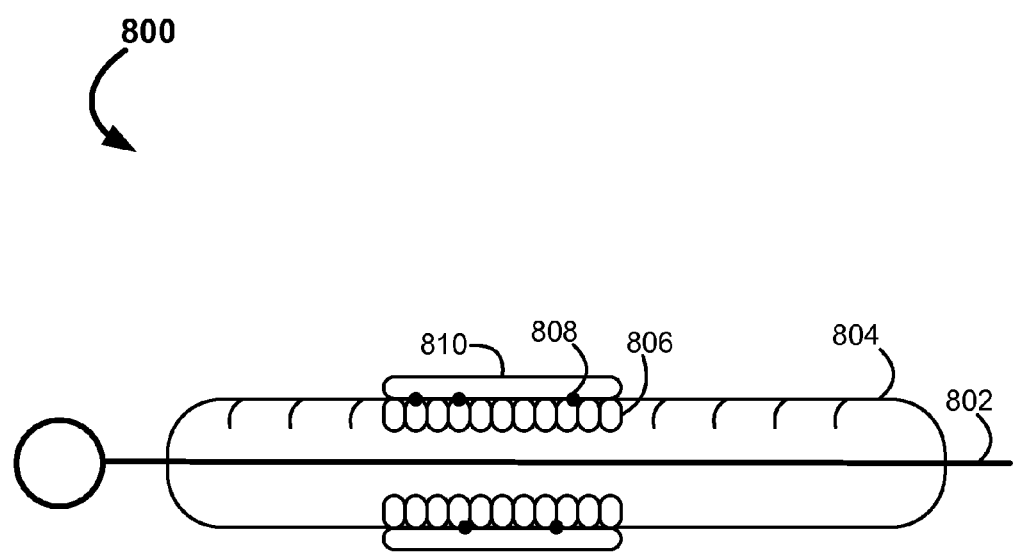
FIG. 8 is an example schematic diagram for a catheter system for novel therapies using the improved medical device, in accordance with some embodiments.

Cells that repair in the brain can migrate, so migration is a better practice than injection. FIG. 8 is an example schematic diagram for a catheter system being utilized for such a novel therapy using the improved medical device, shown generally at 800. This catheter system may include a guidewire 802 for placement of the catheter system. The catheter tube 804 may include position markers. A therapeutic section of the catheter delivers cells is implanted at a particular target depth in the patient. Imaging and radio-opaque dyes may be further utilized in order to better position the therapeutic region of the catheter.

The therapeutic section of the catheter may have a similar geometry as discussed above in relation to FIGS. 1-3. The luminal layer 806 of the therapeutic region may include ependymal epithelium, but could alternatively be a non-biological porous material for practicality, or cost saving, purposes. The layer 806, regardless of biological activity, is configured to prevent cells or other medication to migrate into the CSF, but would allow the passage of any growth factors or signaling proteins to reach the stem cells 808 via pores that are smaller than cells 808 themselves. The abluminal therapeutic section 810 would contain an absorbable and permeable section to allow the stem cells to migrate into the tissue. This therapeutic section 810 may include a porous matrix, as previously disclosed, or any other appropriate material. In some embodiments this therapeutic section 810 may be designed to slowly degrade when implanted in order to further promote stem cell migration into the surrounding tissue.

Additionally, the therapeutic section 810 may include medication with, or in place of, the stem cells 808. These medications may include, for example chemotherapeutics, growth factors, brachytherapy, or the like. In fact, by changing cell or medication constituents, it is possible to deliver cells and/or medications this way to any organ system, but the current design is especially useful for the brain and spinal cord, since it allows CSF flow to areas of injury and cellular migration and repair.

Figure 9:
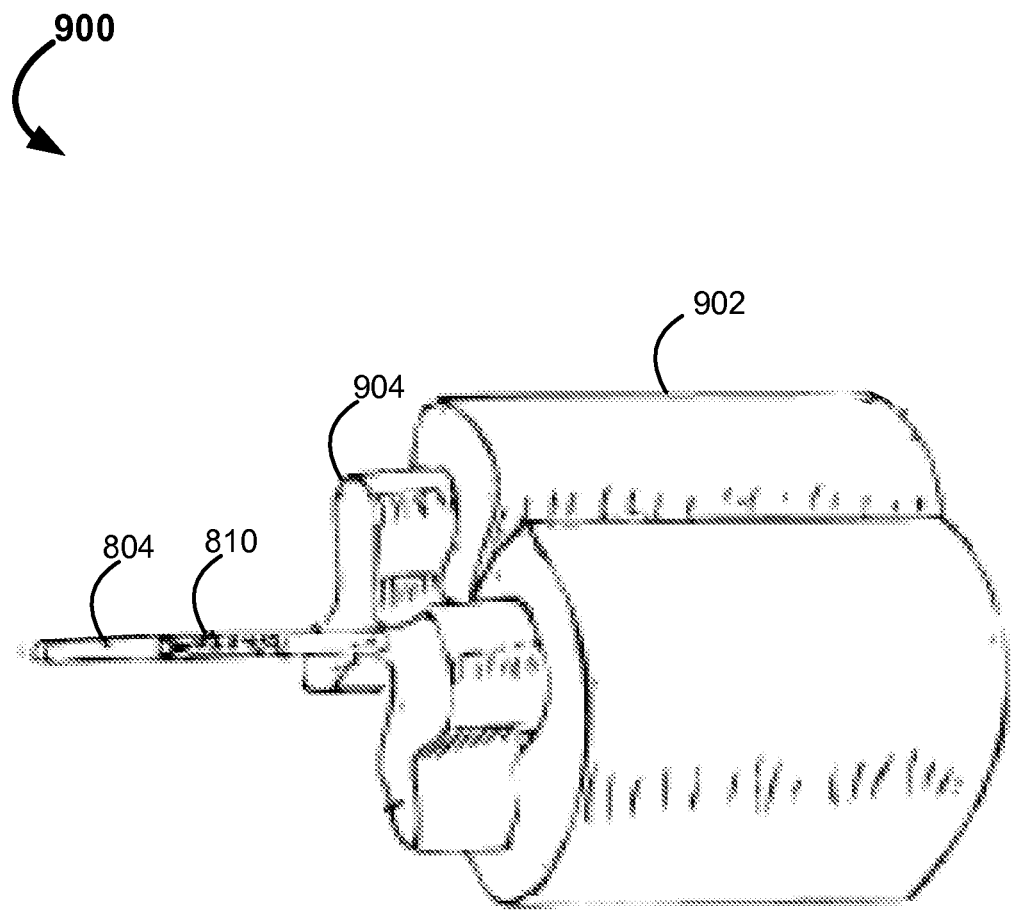
FIG. 9 is an example illustration of the catheter system being utilized as for novel therapy, in accordance with some embodiments.

Moving to FIG. 9, an example illustration of the catheter system 804 being utilized as for such a novel therapy is provided, shown generally at 900. In this example illustration, a synthetic central canal connects two endogenous central canals disrupted by injury or repair. A 'catalyst' for repair would be achieved by preseeding a tissue engineered ependyma on the central canal area on such a 3D matrix construct such that two separated regions of spinal tissue could be connected via the respective central canals, restoring CSF flow and a reparative endothelium, where subependymal stem cells could guide repair of in-growing nerves, blood vessels and glia. Indeed, neurogenesis has been reported from the ependymal region. Similarly, gliogenesis near the central canal includes the generation of ependymal cells, reactive astrocytes, oligodendrocyte precursors and microglia. Moreover, in development, injury and disease, basal processes of the ependyma have been noted to form extensive interdigitations with axons and guide axons during development and regeneration.

III. Novel Bioreactor

While much of the discussion has centered on the usage of the medical device usable in a patient for therapeutic purposes, the instant medical device also has utility in extracorporeal uses, such as for research purposes and external therapies.

Cells behave differently in a Petri dish (in vitro) vs. an actual body (in vivo). One important factor is shear stresses, such as CSF flow pathways or blood flow. Endothelial and epithelial cultures behave differently when placed in flow chambers, comprised on fluid conduits and pumps that deliver a flow similar to physiological conditions. Some bioreactors mimic the blood brain barrier, or have utilized astrocyte cultures to study foreign body reactions including the occlusion of shunts.

Placing the present medical device in such a physiological mimicking bioreactor may provide unique opportunities for higher fidelity research and therapies, including studying of the brain/CSF barrier, cell-cell interactions, cell-matrix interactions, cell-soluble factor interactions, cell-transmembrane protein interaction, interaction and production of extracellular matrix compounds, cellular signaling, cellular migration, cell-fate analysis, the effects of toxins/infectious agents including viruses and bacteria/drugs/blood/proteins/foreign bodies/radiation/nutrional/metabolic/oxidative/hyperbaric stresses on cell behavior, production and processing of CSF, production of growth factors, and production of cells, including neurons, astrocytes, ependyma, oligodendrocytes, microglia, etc., along with tissue and organ development and maturation, among others.

This bioreactor would provide a higher sensitivity and higher throughput system for research and therapeutic design. The system incorporates multiple wells where the ependymal substrate could be subjected to visualization through time-lapse or real-time confocal microscopy, radiation, oxidative, metabolic and mechanical stresses, dose responses and chemical gradients and cell-sorting in a reproducible system. Such a system would allow studies of the ependymal stem cell niche, stem cell programming, along with studies of neurotransmitters, inherent enzymatic processes and secretions of the ependyma, neuroactive peptides, barrier function of the ependyma and the movement of water across the ependyma. This bioreactor could be combined with other models, such as blood-brain barrier models or models of neuronal circuits, thus resulting in high fidelity simulation of the nervous system useful for research and therapeutic design.

A. System

A anthropomorphic CSF pathway would comprise the best flow chamber to simulate shear forces. Such anthropomorphic CSF pathways could be the 3D shape of the ventricular system, or the S shaped geometry of the spine, along with dura, arachnoid, nerve roots, dentate ligament simulations for higher fidelity representation of the CSF pulse and flow, for example. One or more oscillatory pumps could circulate fluid under computer control and simulate the effects of the cardiac, respiratory, cough/valsalva or body positional changes on pulsatile and oscillatory CSF hydrodynamics. The pumping may directly influence the CSF flow by the introducing and removing fluid from the simulated subarachnoid space. Alternatively, the pulsatile pump could introduce fluid into simulated subarachnoid vessels, of which the systolic and diastolic variations in vessel geometry could secondarily translate into movement of CSF. The pumps could be under control of computer models of physiological and pathophysiological processes for unprecedented accuracy. Other reservoirs, pumps and valves could simulate the production and absorption of CSF, which comprises the bulk flow of CSF. A plurality of ports and sensors/and transducers could feedback into the computer control to maintain homeostasis and simulate disease states. The cells, tissues and micro-organs would be subject to similar biomechanical forces as in the body, through the motion of the fluids as well as mechanical movements of the matrix. As such, the cells, tissues and micro-organs would react and develop in a high-fidelity simulation environment.

Figure 10:
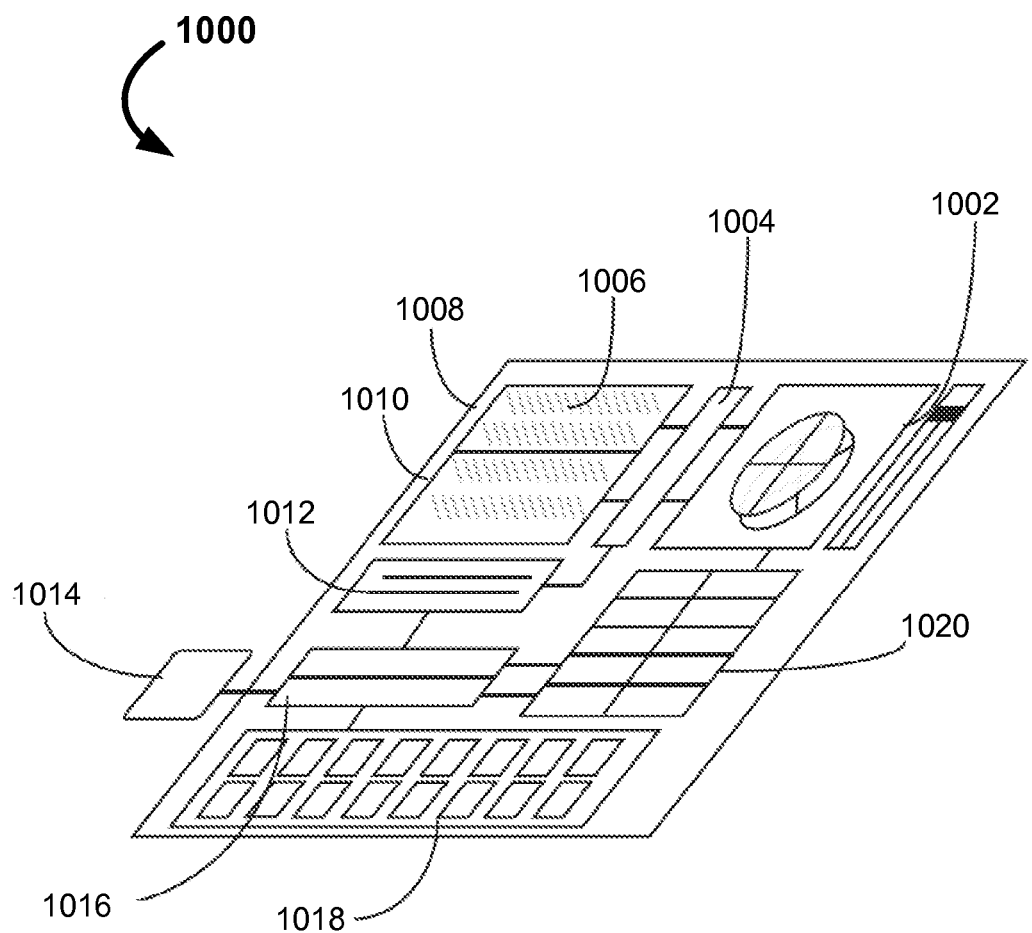
FIG. 10 is an example schematic diagram for a microfluidic system useful in conjunction with the improved medical device, in accordance with some embodiments.

To maintain the tissue of the medical devices located in the bioreactor, each tissue module may have its own microfluidic circuit to regulate the local environment, deliver growth factors or sample the local environment. FIG. 10 is an example schematic diagram for a microfluidic circuit 1000 system useful in conjunction with the improved medical device. The microfluidic circuit 1000 may provide for nutrients and waste disposal via onboard microfluidic pathways and pumps and sensors. Additional circuits and reservoirs could sample and collect signaling proteins from the microenvironment or even guide nascent cells into collection chambers utilizing cell-sorting techniques, which may be chemical, mechanical, acoustic or radiative. This illustrated microfluidic circuit 1000 may be a micro-electrical mechanical system (MEMS) generated using lithography from a silicon wafer, or may employ other manufacturing techniques. While a particular microfluidic embodiment is illustrated herein, additional microfluidic circuit designs are equally employable.

In the present microfluidic circuit 1000 a micropumping system 1002 may provide localized drug delivery, including growth factors, and the like. A micro analyzer 1004 may provide feedback regarding the tissues condition. The micro analyzer may include chemical sensors, conductivity sensors, spectrophotometers, or any other applicable analyzer. An array of micro-needles 1006 may include sensors, transducers, or a load cell assembly. There may be in and out microports 1008 and 1010 respectively, which enable the sampling of tissue fluids, and a pathway for drug delivery.

A processor 1012 may control the sensors, pumps, valves, etc. of the microfluidic circuit. An additional reservoir 1014 may store specimens, or exogenous therapeutic substances. Such specimens can be further utilized to study cellular signaling through gene expression (DNA, RNA, antibodies and immunochemistry assays). Additionally, there may be one or more therapeutic substance reservoirs 1016 as well. As such, the microfluidic system can deliver drugs or proteins to the system to effect the behavior of the system. An energy transducer 1018 under computer feedback can sense tissue, and a microfiltration system 1020 can heat cool and sort samples. The microfiltration system may employ mechanical, chemical, cellular or tissue filters. This enables the capture of progeny cells of the subependymal stem cells. Cells may then be sorted by flow cytometry, impedance, laser, ultrasound, chemical sorting, antibody and/or utilize real-time high resolution video camera.

Figure 11:
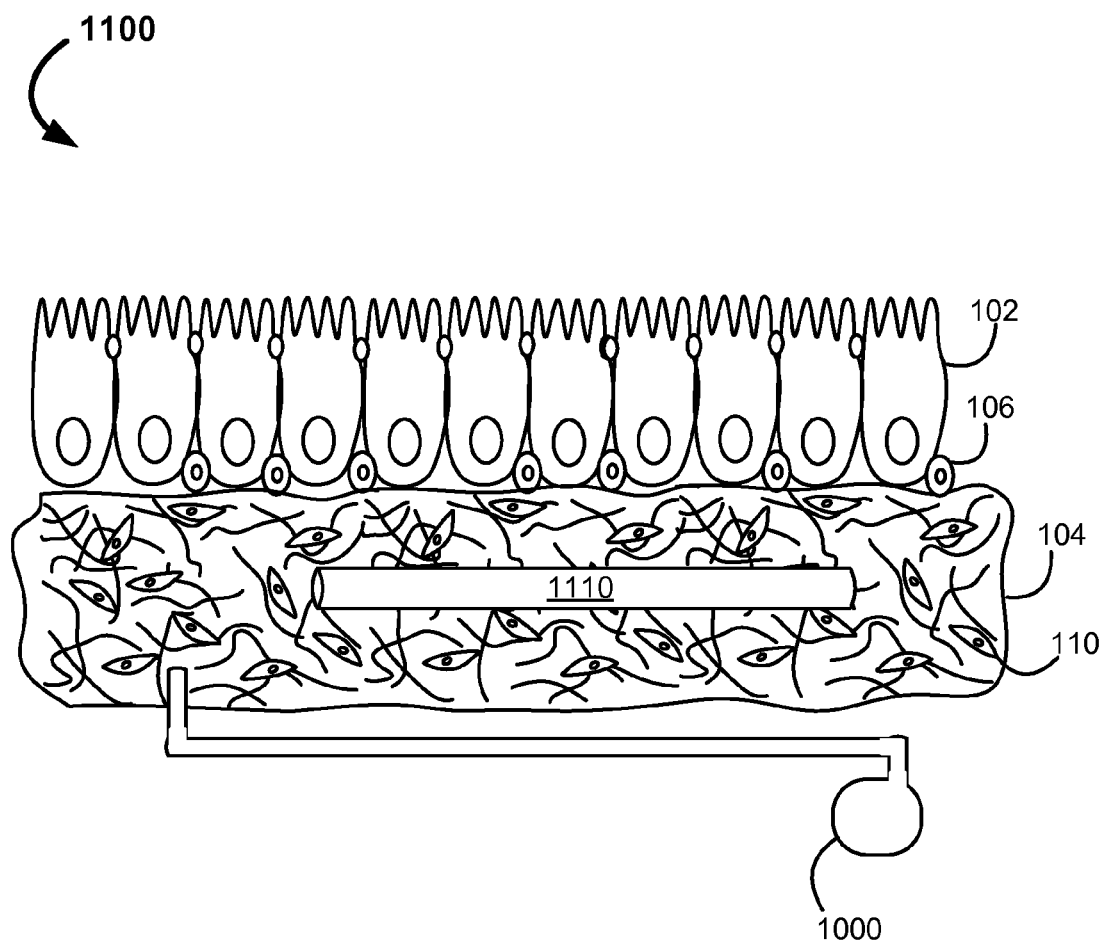
FIG. 11 is an example cross sectional view of a vascularized embodiment of the improved medical device, in accordance with some embodiments.

The microfluidic circuit 1000 may couple to the medical device to form a bioshunt 1100 that may be inserted into an anthropomorphic bioreactor. FIG. 11 is an example cross sectional view of the bioshunt 1100, which as previously mentioned may include a vascularized embodiment of the improved medical device, in conjunction with the microfluidic circuit 1000. The bioshunt 1100 includes many elements of the medical device already discussed, including the ependymal and/or choroidal epithelium 102, subependymal stem cells 106 along a 3D matrix 104 for studies of cellular migration or signaling. Tanacytes or cirumventricular organs are includable in some embodiments. Other cells 110 such as neurons and other glia and endothelial cells and astrocytes simulating the blood brain barrier may also be included.

In some embodiments, one or more blood vessels 1110 may be included within the matrix 104. An in/out port for real or simulated pulsatile blood flow may be included in these embodiments (not illustrated), along with perivascular spaces, such as Virchow-Robin space, to simulate perivascular fluid flow. Models that change alter the perivascular flow by valve or diaphragms are useful for studying hydrocephalus as it may entail some decoupling of the vascular and CSF flow through the perivascular spaces. In some embodiments, a specialized version of the model would feature the ependyma/choroid and blood flow to simulate CSF production. The blood vessel, when present, may consist of a void within the matrix 104. This void may be lined with smooth muscle cells, endothelialithelial cells, fibronection a synthetic membrane, or may merely be unlined (matrix material would then come into contact with blood of other fluid).

Figure 12:
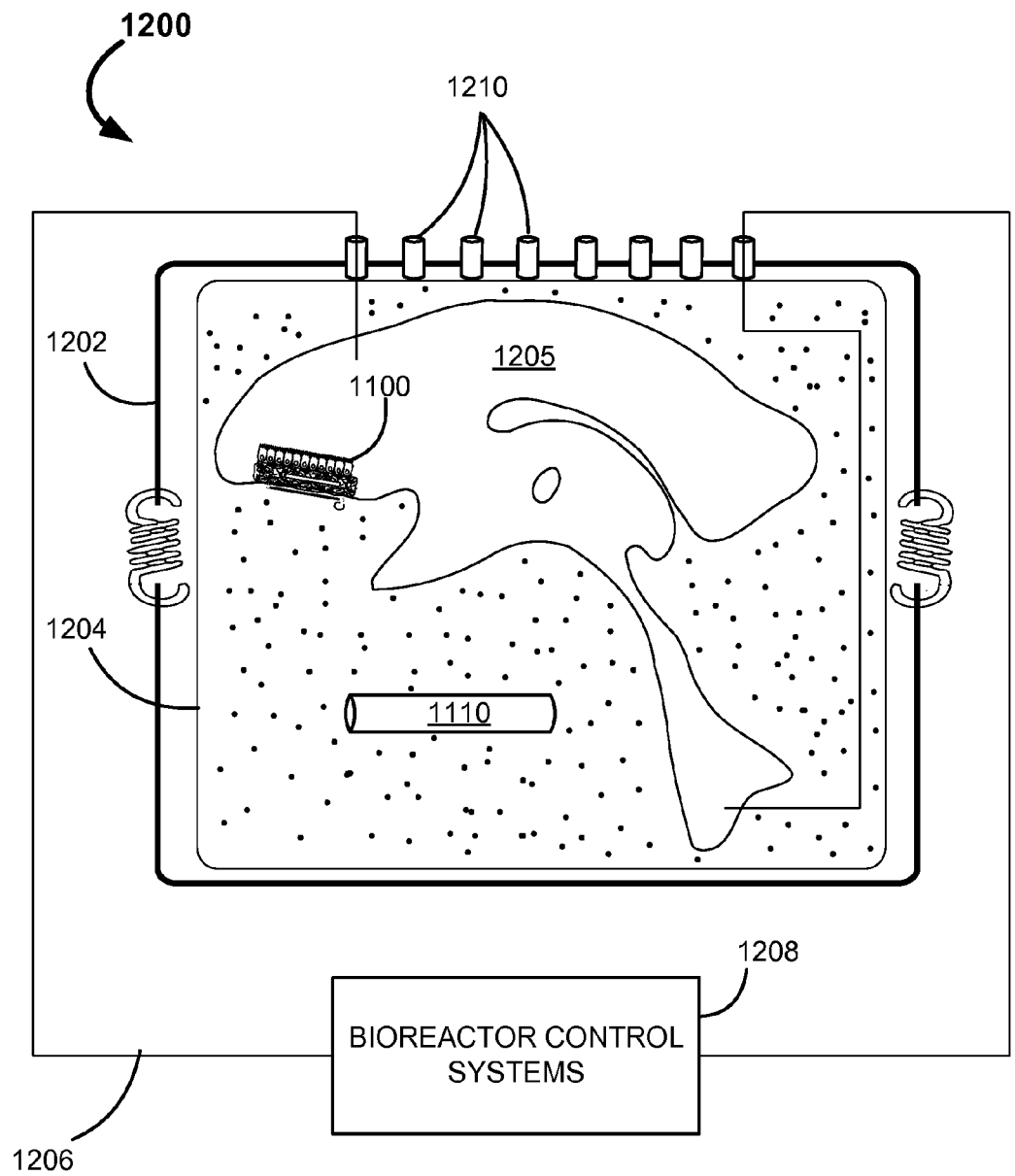
FIG. 12 is an example schematic diagram for an enhanced physiological mimicry bioreactor used in conjunction with the improved medical device, in accordance with some embodiments.

On example of an anthropomorphic bioreactor is illustrated in example FIG. 12, shown generally at 1200. The bioshunt 1100, in some embodiments, may be placed along the flow chamber in a number of geometries, such as flat slides, multiple sheets of cells, tubular and/or 3D shaped structures and/or multiple tubules in serial and parallel orientation. The basic bioshunt 1100 unit can be multiplied many times in multiple chambers on the bioreactor to create a way of doing high throughput testing for drugs or foreign body reactions to chemical materials in medical device design or basic studies of physiology or pathophysiology, including hydrocephalus, Alzheimer's disease, multiple sclerosis, etc. In this example bioreactor, a cranial model with rigid, articulating skull panels 1202 contains a flexible brain model 1204 with ventricular system 1205. In some embodiments, blood vessels are embedded within the soft tissue model 1204 to simulate the blood flow loop in a fixed container. A computer controlled pump can send pulsatile blood volumes and returned via venous system, which can obstructed to simulate pathologies in which venous obstruction and CSF outflow pathways are blocked. Other embodiments could focus on the spinal anatomy or combination brain and spinal anatomy or other anatomic and physiological systems.

Figure 22:
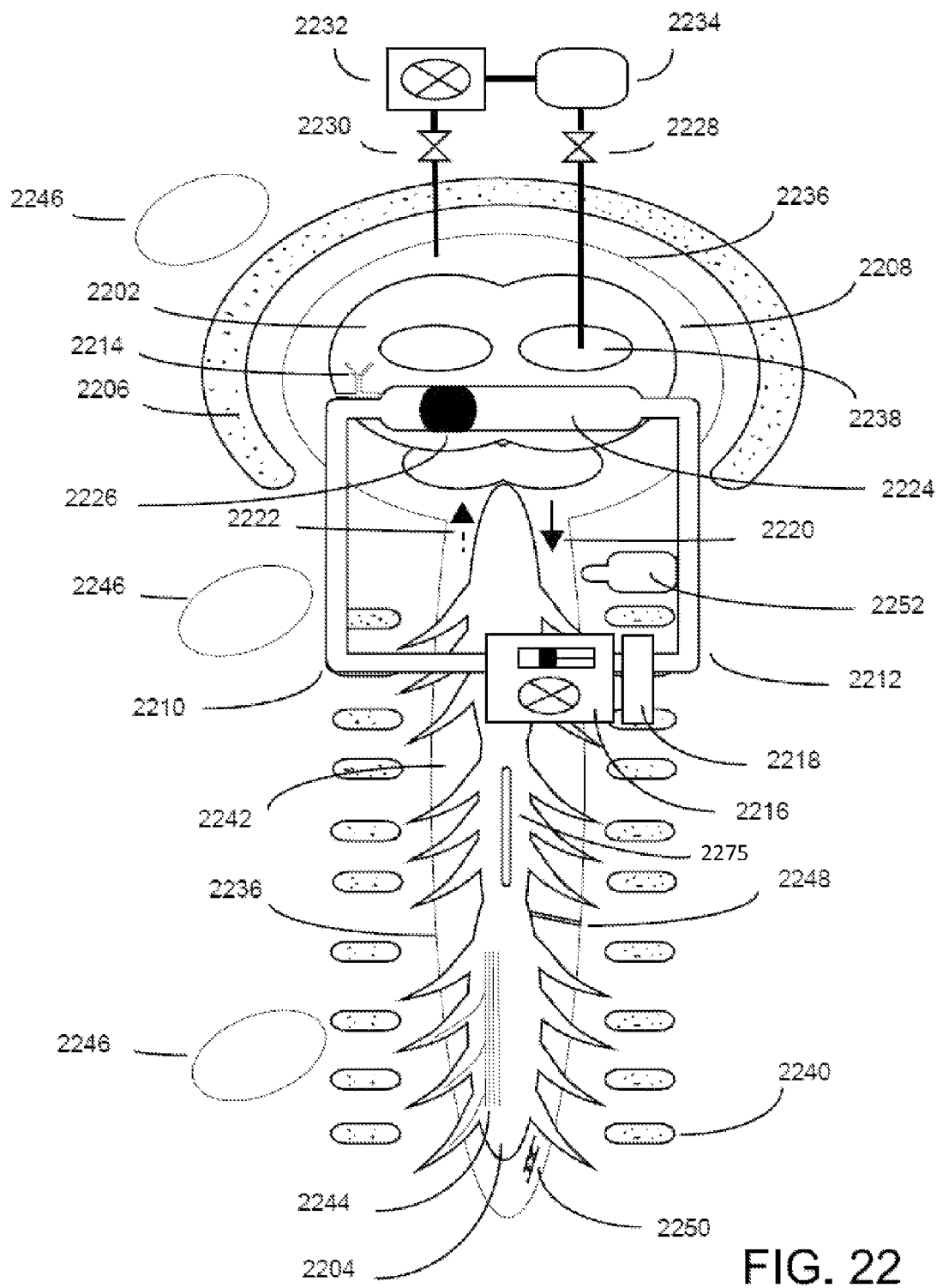
FIG. 22 is an example schematic diagram for an anthropomorphic cerebrospinal model, in accordance with some embodiments.

For example, FIG. 22 shows an anthropomorphic cerebrospinal model with vascular coupling. A skull model 2206 envelops a flexible, puncturable and replaceable dural model 2236, which contains a brain subarachnoid space 2208 and spinal subarachnoid space 2242. The soft tissue model can be made of silicone or other similar material. The subdural space contains a flexible brain model 2202 and spinal model with nerve roots and sleeves 2204. A plurality of wires can be transmitted through the brain and spinal/nerve root model to mimic the flow of electromagnetic radiation 300. A plurality of interventional or surgical sites 2246 allows access to the deep structures of the model. The subdural space transmits the cerebrospinal pulse and flow waveform. In addition to the nerve roots and sleeves, additional fasteners mimicking the dentate ligaments 2248 or arachnoid membrane 2250 can be added. These supporting structures are thought to influence the harmonics of the cerebrospinal pulse and flow waveform.

Embedded within the brain model 2202 and/or spinal model 2204 are fluid conduits mimicking cranial blood vessels 2226 and/or spinal blood vessels 2275. Blood vessels are made of silicone or any similar material. Perivascular spaces 2214 allow the flow of CSF into the substance of the brain and/or spinal cord. A waveform generating pump propels fluid into the embedded vessels. The inflow conduit 2210 conducts fluid in a physical windkessel model 2224, which mimics the arterial, arteriolar, capillary, venule and venous system. An elastomeric cuff or valve 2226 alters blood flow into the windkessel model and can simulate the autoregulation of blood flow into the brain. The elastomeric cuff can be computer, computer model or operator controlled. The return conduit 2212 sends fluid back to a reservoir 2218 and the waveform generating pump 2216. A computer or operator controlled expanding bladder or mechanical occluder 2252 can mimic the effects of venous obstruction on cerebrospinal dynamics, as can a computer or operator controlled CSF outflow valve 2230.

With the systolic and diastolic actions of the waveform generating pump 2216 and flow through the conduits, there is expansion of the vessels within brain model, which causes the brain model to expand in the fixed cranial cavity, thereby displacing a volume of cerebrospinal fluid into the spinal compartment. During systole, the flow of CSF is depicted by the downward arrow 2220. During diastole, the flow of CSF is depicted by the upward arrow 2222.

Cerebrospinal fluid production and absorption are modeled, as well. A CSF reservoir 2234 sends fluid via pump or gravity drainage through a computer or operator controlled valve 2228 into site of CSF production, such as in the ventricular lining. Cerebrospinal fluid absorption is modeled via a computer or operator controlled valve 2230 that features a pop off opening pressure. Such as in the arachnoid granulations, a pressure of approximately 5 mm Hg, the pressure of the dural venous sinus, must be overcome for CSF drainage to take places. CSF outflow resistance can be regulated and modeled in with this mechanism. An optional pump sends CSF back to the reservoir 2234 to conserve fluid. Cells or tissue can be embedded along the dura, pial, parenchymal or mesenchymal brain or ventricular model or along the spinal model and vasculature, etc. Normal and diseased states and processes can be modeled through alterations in cerebrospinal production and absorption along with changes in cerebrospinal pulse dynamics and their effects on cells.

A plurality of detectors (pressure and flow sensors, etc.) can be placed along the model and interface with a control system to influence actuators (pumps, valves, etc.) to simulate normal and diseased states and processes and feedback loops.

Returning to FIG. 12, the CSF is comprised of two (2) flows: bulk and pulsatile. The bulk flow is the production and absorption of CSF, which could modeled with an IV drip for inflow and a check valve for absorption, for example. A series of ports 1210 along the flow chamber allow for CSF addition or removal in a way that mimics bulk flow. Additionally, the ports 1210 may enable sensors and transducers to sample the CSF and provide feedback into the bioreactor control systems 1208 to maintain homeostasis and, where desirable, simulate a disease state. The ports 1210 can also introduce surgical tools or endoscopic equipment. The ports can be configured to allow microscopy and/or camera equipment.

An oscillatory pump under computer control, as part of the bioreactor control systems 1208 generates the pulsatile flow to simulate the CSF and/or vascular system. The oscillatory pump may be enabled to simulate cardiac, respiratory, cough/valsalva or body positional changes on CSF hydrodynamics. A fluid path 1206 may couple the bioreactor control systems 1208 to the bioreactor. The pumping cycles and fluid entry and egress can be controlled by a software model of the physiology and pathophysiology. (Adapted from Radojicic patent application Ser. No. 12/857,555, which is hereby incorporated by reference). For example, an external cardiac waveform generated by a software model or an actual EKG or echocardiogram could be analyzed with a mathematical transfer function programmed into the embedded computational circuitry to produce an expected cerebrospinal fluid flow based on the cardiac output. Thus, the computational circuitry could alter the flow and cycle of the pump to mimic physiological states. Additionally, alternative embodiments of the system may include computational circuitry that identifies the components of the pulsatile intraspinal or intracranial pressure and then gate the opening of a cerebrospinal fluid valve, which regulates CSF outflow, according to the cardiac and/or respiratory cycle or body position. Thus, both alterations in CSF pulse and flow and simulated arterial pulsations within the matrix contribute biomechanical stresses that influence the cells and provide a realistic simulation environment. Key variables that are monitored for models may include temperature, pressure, flow, glucose levels, lactate levels, pH and oxygen and carbon dioxide levels.

Figure 13:
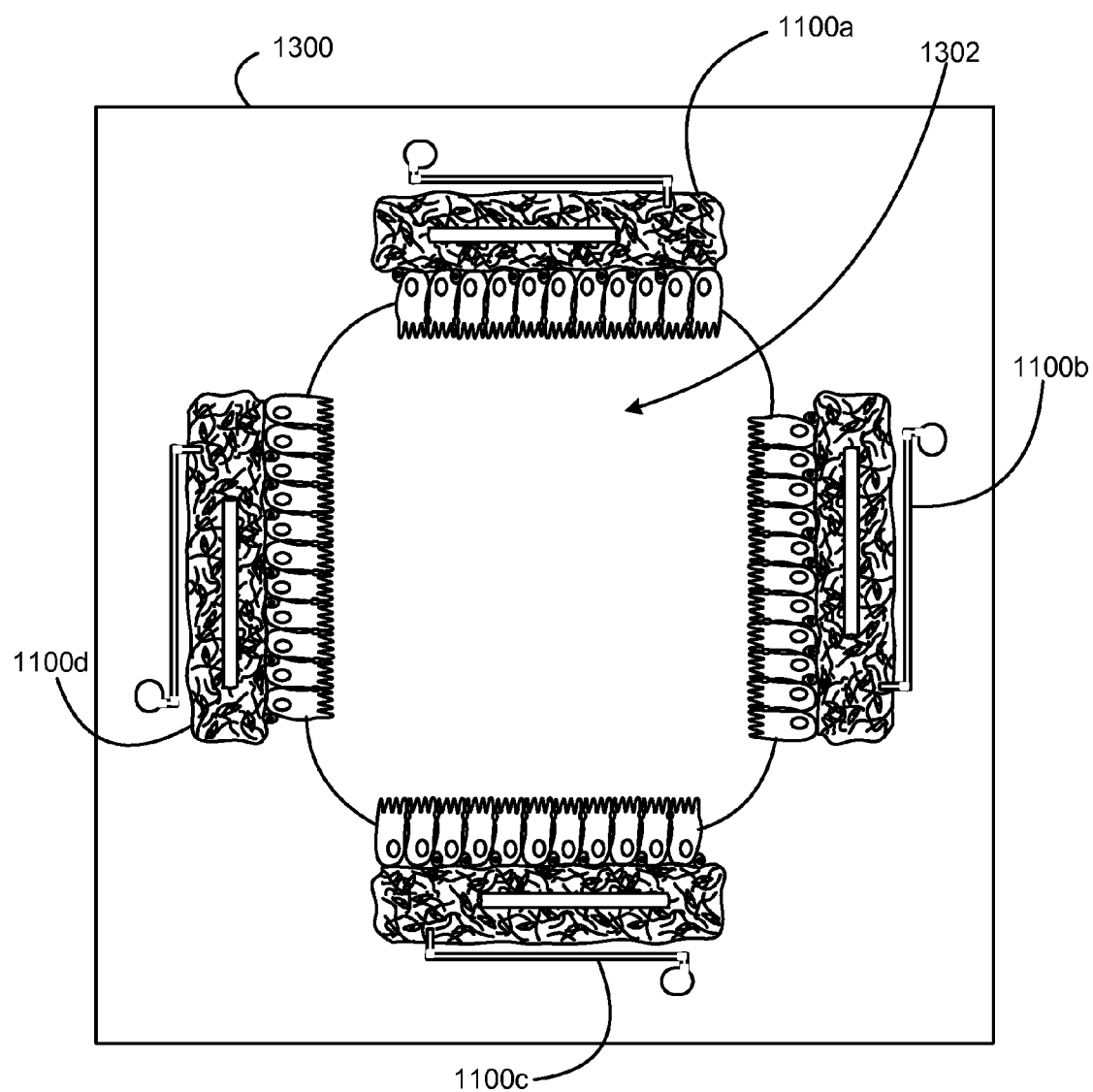
FIGS. 13 and 14 are example diagrams of cross sectional views of enhanced physiological mimicry bioreactors used in conjunction with the improved medical device, in accordance with some embodiments.

Other bioreactor designs are also possible. For example, FIG. 13 illustrates a cross sectional view of an example bioreactor 1300 which includes four (4) bioshunts 1100a to 1100d, surrounding a central CSF filled lumen 1302. This illustrates that the basic unit of the CSF bioreactor, the bioshunt 1100 which includes a microfluidic circuit, may be multiplied around an artificial CSF pathway in any manner desired for therapeutic, diagnostic or research purposes. This further enables high throughput testing drugs or foreign body reactions to chemical materials in medical device design.

Figure 14:
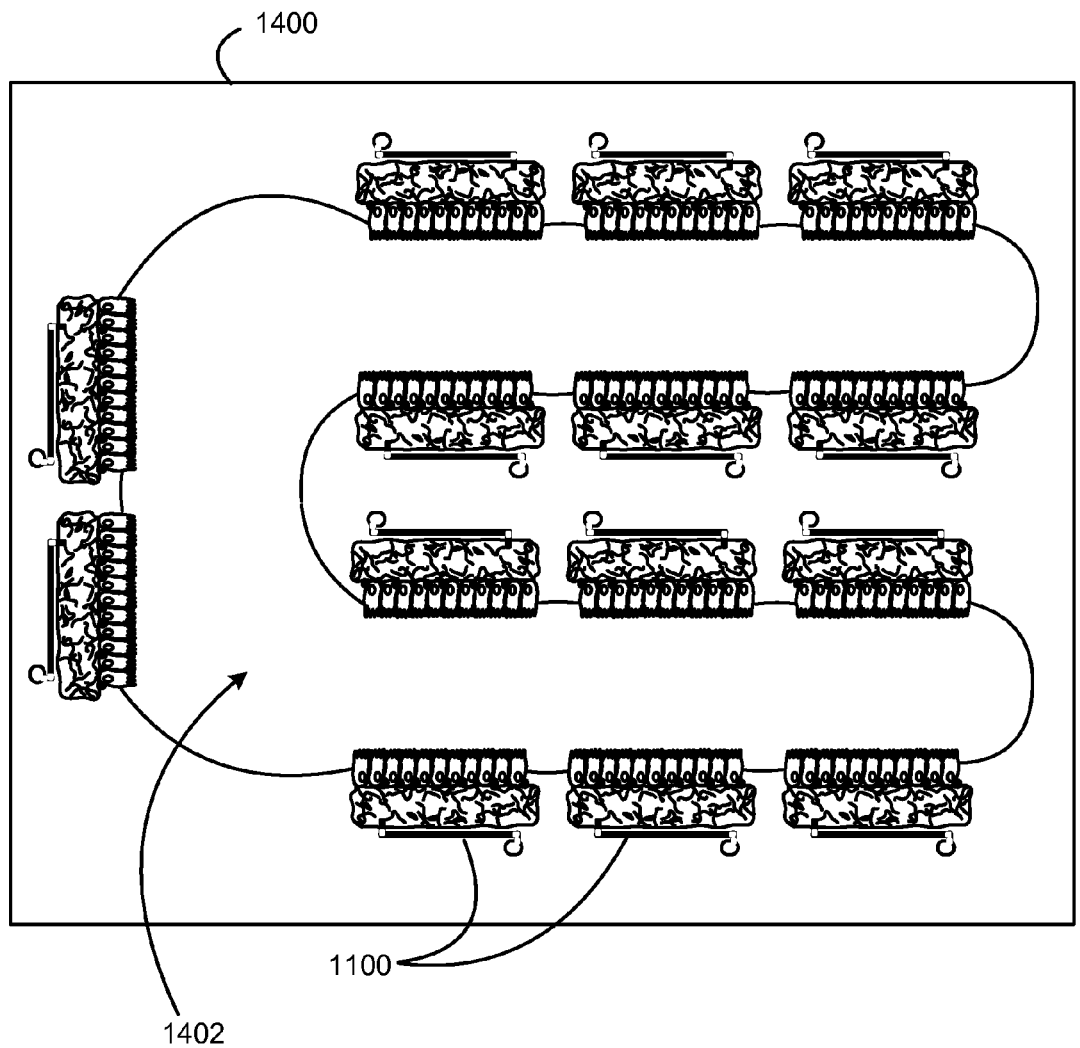

Likewise, FIG. 14 provides yet another cross sectional view of an example bioreactor 1400 which includes twelve (12) bioshunts 1100, surrounding a complex 3D shaped CSF filled lumen 1402. This type of complex bioreactor allows for high throughput testing of drug compounds, ideal microenvironments, improved growth factor recipes, anthropomorphic or tailored shear stresses, brain/csf barrier modeling, etc. The shape of the bioreactor may be comprised in a plurality of bioshunts 1100 in 2D or 3D sheets or tubules, or even more complex geometries, in series or parallel. Additionally, these ependymal bioreactors can be combined with other models of the blood/brain barrier or other brain tissue substrates.

Figure 15:
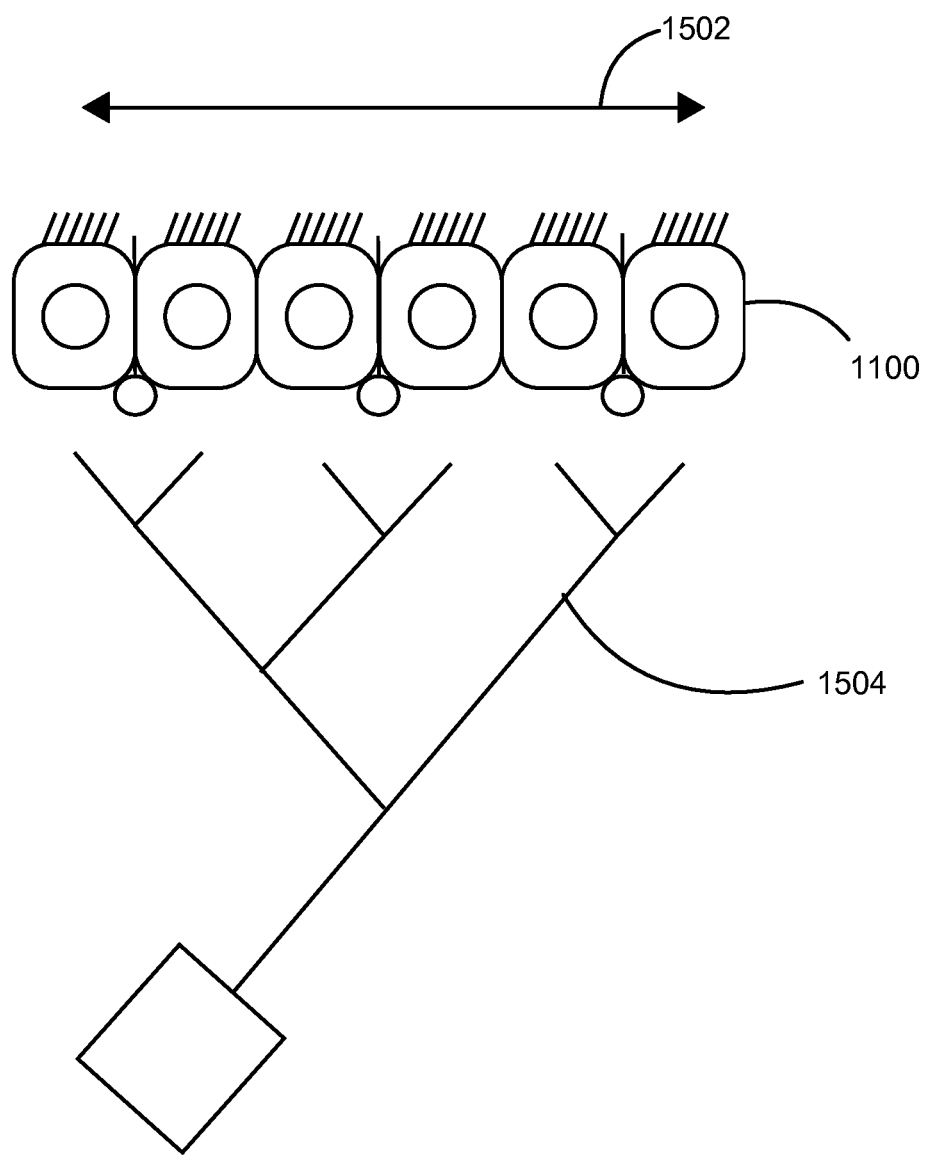
FIG. 15 demonstrates how CSF flow and a matrix capillary microfluidic network is utilized to both study and influence the cells and tissue construct.

FIG. 15 demonstrates how pulsatile and oscillatory fluid flow 1502 can influence the tissue construct 1100. Likewise, a matrix capillary microfluidic network 1504 can be utilized to deliver drugs including gradients to influence cells. The capillary network can be synthetic or bioactive including fibronectin and endothelial cell lining. Similarly, the capillary network can be utilized to sample the local microenvironment to study cell-cell interactions, cell-matrix interactions and cell-soluble factor interactions. Advanced embodiments will include microchannels for guiding progeny of subependymal cells into reservoirs for cell fate analysis as well as industrial production of cells, the lineage of which can be influenced with the spatial and temporal signaling made possible by this device. The bioreactor could therefore become a cell producing factory where cells are captured along fluidic circuits incorporated into the 3D cell culture. The pumps and valves are computer controlled and can simulate normal physiology, injury and disease states with computer models that receive input from detectors on model and can process the feedback.

Figure 16:
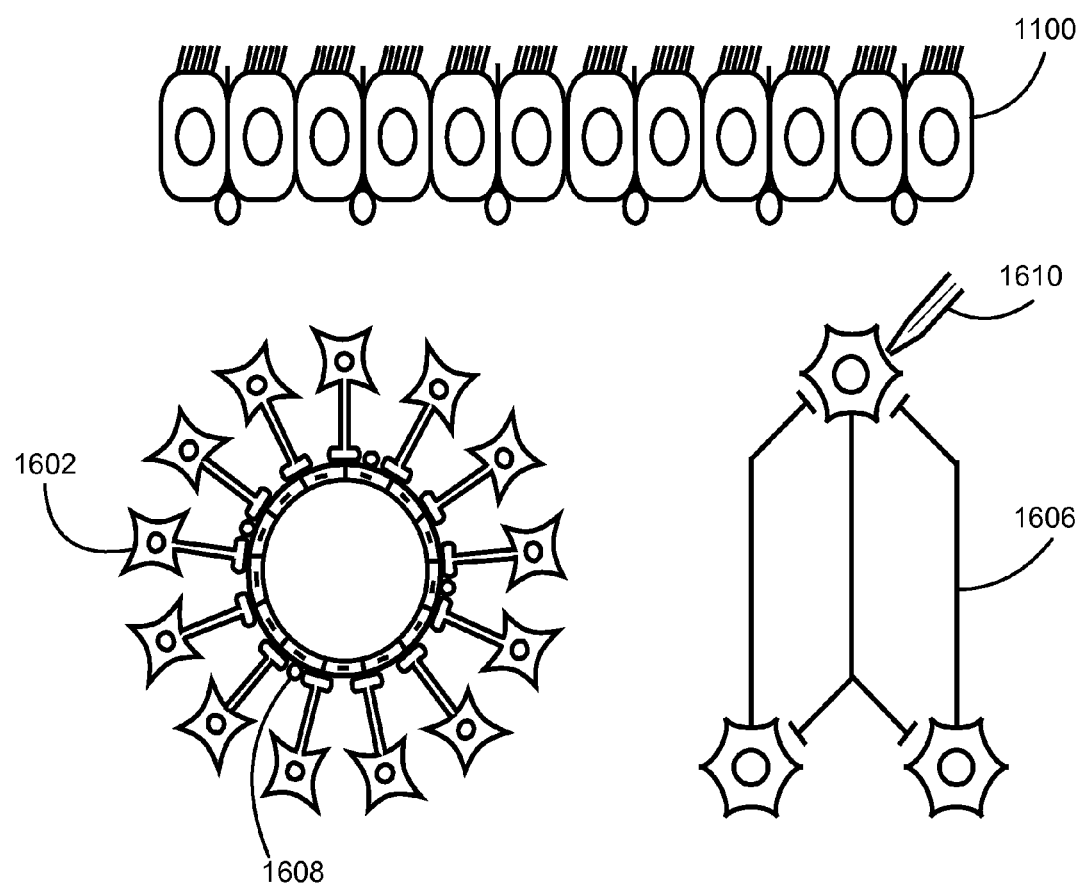
FIG. 16 demonstrates the ependymal bioreactor used in combination with other models of nervous system function, including blood-brain barrier models and models of neuronal function.

FIG. 16 demonstrates the ependymal bioshunt 1100 utilized in a bioreactor in combination with other models of nervous system function, including models of the blood-brain barrier 1602 where astrocyte foot processes about endothelial, smooth muscle and perivascular stem cells 1608, as well as models of larger vessels such as arterioles. A novel addition to this model would be a pressure sensing matrix, where the vasospasm or fluid stresses could be assessed, as well as, the effects of subarachnoid blood on scarring of the ependyma can be studied, as well as the effects of particular blood products on vasospasm, useful in designing novel therapies. Additionally, the ependymal bioshunt 1100 could be used in conjunction with neuronal models of electrical, magnetic, ionic, receptor and/or neurotransmitter transmission, including patch clamping and clamp arrays 1610 and general stimulation with a wire. As such, this combination produces a high-fidelity simulation of the nervous system for research and therapeutic design. Non-limiting areas of study and therapeutics include intrathecal drug delivery and pumping systems, novel shunting systems and foreign body reactions, the effect of blood products and inflammatory mediators in the CSF and brain including vasospasm, which may include culturing vascular analogs on a pressure sensing matrix to study the effect of constituents on vasospasm and mechanisms of tumorigenesis, of which perivascular stem cells 1608 have been implicated. Seemingly disparate brain and spinal disorders may be studied in higher fidelity. Nonlimiting examples include systems and methods that the improve the access, analysis, treatment, diversion and exchange of the cerebrospinal fluid, central nervous trauma, hemorrhage, infections, toxins, metabolic derangements, structural malformations, cystic lesions, benign and malignant masses, imbalances of cerebrospinal fluid production and absorption and flow, neurodegenerative diseases, pain syndromes and neuropsychiatric disorders, as well as pharmacological studies on the CNS and experimental studies of the CSF dynamics.

Figure 17:
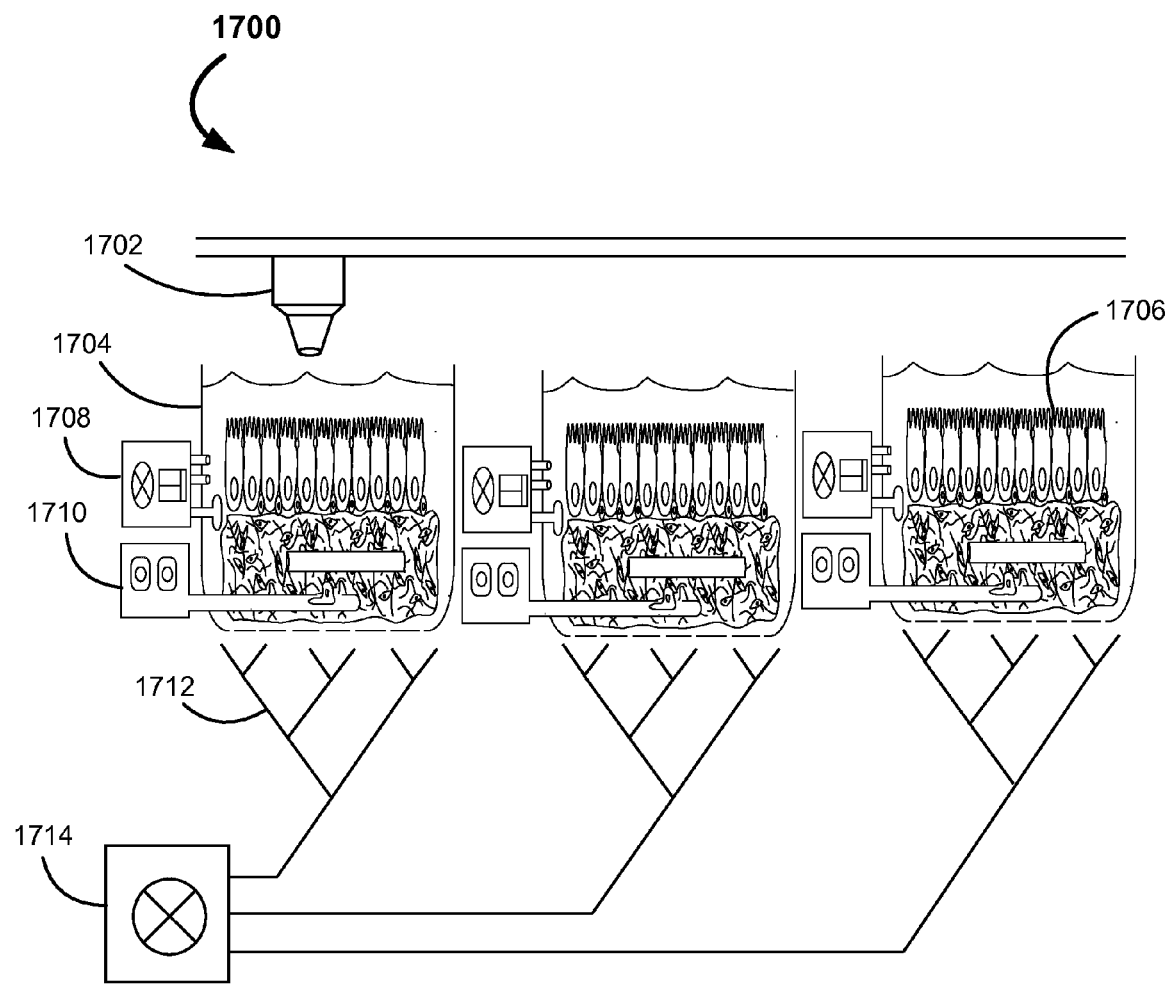
FIG. 17 demonstrates a high resolution, high throughput bioreactor.

FIG. 17 shows a high resolution, high throughput embodiment of the bioreactor. An ependymal lining with subependymal stem cells suspended on a matrix with additional cells and embedded vessels capable of in/out pulsatile flow 1706 is immersed in a microwell and bath 1704 capable of agitation. A scanning device 1702 can be used transmit and collect acoustic or electromagnetic radiation. Nonlimiting examples would include a high resolution camera, confocal microscope, ultrasound probe, photoacoustic probe, raman spectroscopy, optical coherence tomography, infrared differential interference contrast microscopy, infrared or other spectroscopy. The microwell and fluid bath is capable of bulk and pulsatile flow via a pumping system 1708 also capable of mechanical agitation. Embedded vessels on the matrix 1706 are also capable of pulsatile flow mimicking vessel movements in the body and propelling perivascular fluid flow. The subependymal stem cells are known to produce progeny under certain conditions. This model would allow study of the spatial and temporal patterns of signaling that trigger cell-fate and generation certain cells types. Once elucidated, the system could be programmed to produce a particular cell type through the administration of the correct spatial and temporal signals. Cells could be collected in an industrial fashion via a microchannel into a reservoir 1710. Various cell sorting techniques could be utilized including chemical attractants or repellants, electrotaxis, ultrasound or mechanical sorting. High throughput studies of inflammation and tumorigenesis, as well as anti-inflammatory and anti-cancer techniques and therapeutics are possible. A microfluidic network 1712 under control of computer actuated pumping system 1714 allows for delivery to and/or sampling of the microenvironment. The microfluidic network can assist in ascertainment of dose-responses and the creation of chemical gradients. The microfluidic networks could also sample signaling proteins, transmembrane proteins and/or extracellular matrix proteins in a high throughput fashion. In the microwell 1704, any cell or tissue layer in any 2d or 3d orientation is possible, whether single or multiple, serial or parallel.

Figure 18:
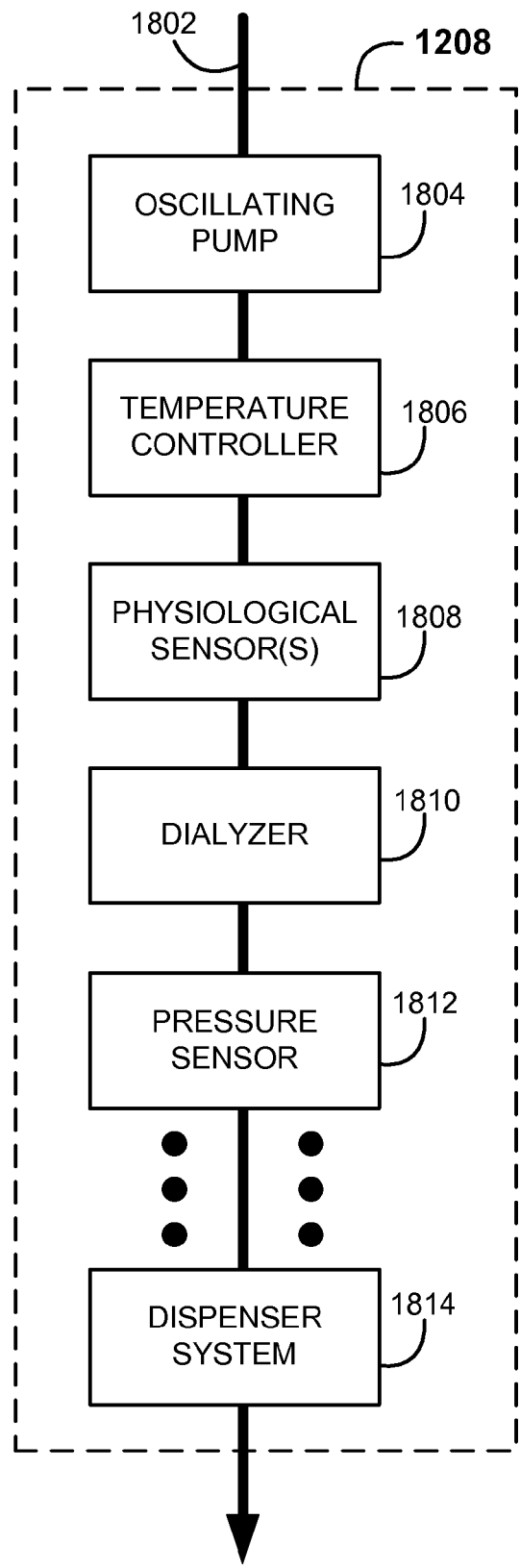
FIG. 18 is an example schematic diagram for the bioreactor control systems used in conjunction with the improved medical device, in accordance with some embodiments.

Continuing, FIG. 18 is an example schematic diagram for the bioreactor control systems 1208 used in conjunction with the improved medical device. The bioreactor control systems 1208 in addition to including an oscillating pump 1804 may further include one or more of a temperature controller 1806, physiological sensors 1808, a dialyzer 1810, pressure sensors 1812, and a dispenser system 1814. A fluid pathway 1802 may couple to one or more of these subsystems as is desirable for a particular procedure. These subsystems may work in conjunction with the microfluidic circuits to more finely control the CSF conditions, and provide the ability to more effectively provide therapy to a patient.

B. Operation and Therapies

Figure 19:
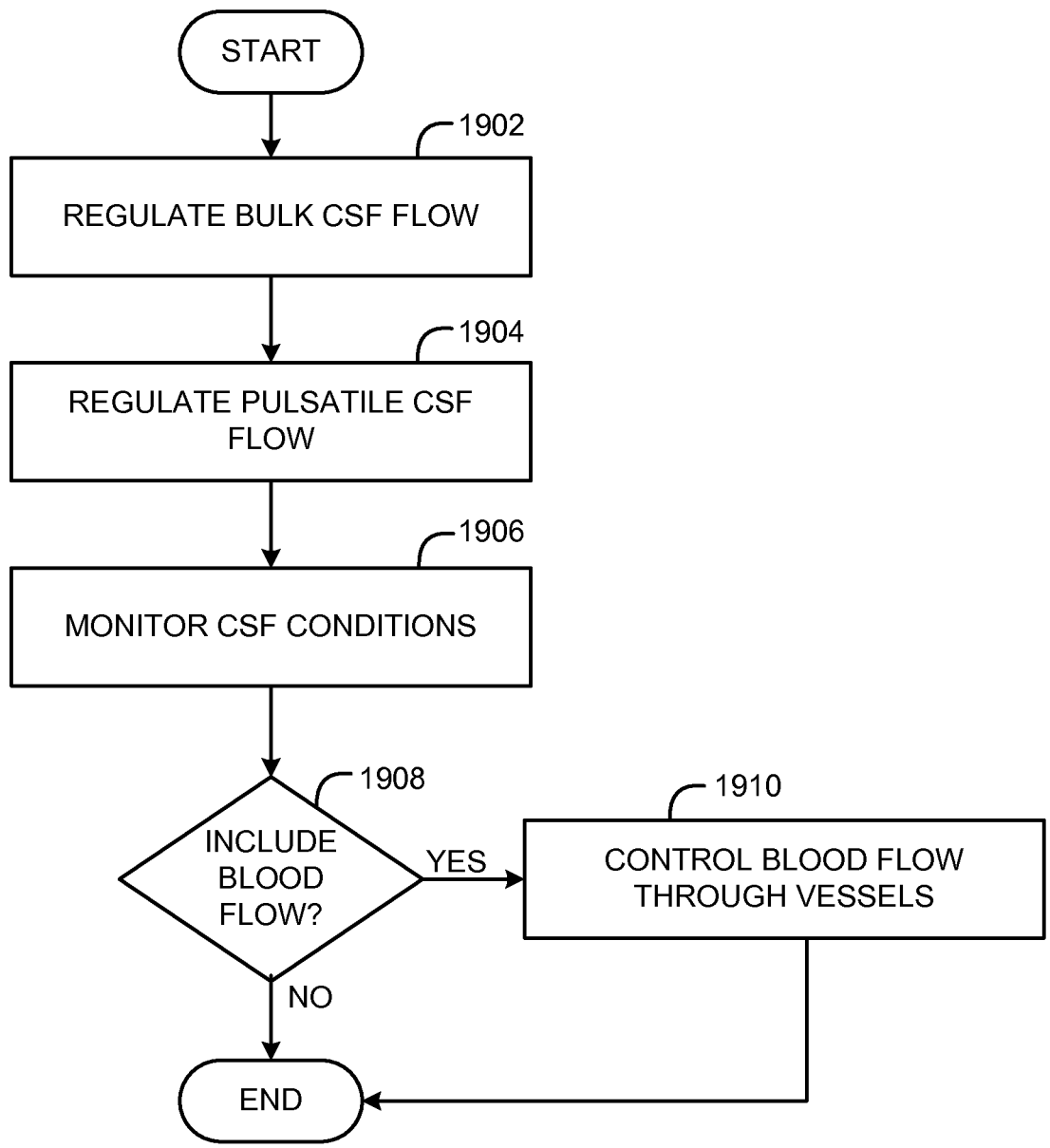
FIG. 19 is an example flow chart for the process of controlling the enhanced physiological mimicry bioreactor, in accordance with some embodiments.

FIG. 19 is an example flow chart for the process of controlling the enhanced physiological mimicry bioreactor, in accordance with some embodiments. In this process the bulk flow of CSF is regulated (at 1902) in order to mimic disease states, or normal physiological functioning. Bulk flow, as previously discussed, may be controlled via check valves, IV drips, or static pumps via the plurality of ports located along the novel bioreactor. In addition to the bulk flow, the control system may regulate pulsatile CSF flow (at 1904) using an oscillating pump. Again, normal or disease states may be mimicked, as desired for any particular application.

The CSF conditions, and the tissue conditions, may be monitored (at 1906) with a plurality of sensors that sample any of CSF temperature, pH, osmolality, tonicity, compositions, electrical properties, spectrographic properties, and any additional measures of interest. Likewise, the tissue of the bioshunt may be monitored using the microfluidic circuit for additional parameters.

If blood flow is included in the bioshunt (determined at 1908), then the blood flow within these blood vessels may be controlled (at 1910). Blood may be provided from the patient directly, or collected (or otherwise synthetic) blood may be utilized. The system may be further coupled to an oxygen exchange unit, and/or other physiological mimicking systems, in order to ensure that the blood remains properly oxygenated, proper temperature, etc.

Some neurodegenerative disease states, such as Alzheimer's disease, are characterized by a deficiency in CSF production. The CSF bioreactor may be configured to model these conditions. Further, in some embodiments, the bioreactor could be utilized therapeutically to produce CSF for a patient off-line or on-line as part of a novel CSF loop, extracorporeally or implanted, via specialized catheters/filaments/micro-needles, etc and pumping systems. The bioreactor could also process/filter the patient's CSF in a biomimetic way and be re-introduced into the system to regulate the tonicity and osmolality/osmolarity of the CSF. Also, the bioreactor may be configured to produce stabilizing and therapeutic proteins, such as growth factors or signaling proteins that a patient's own body no longer sufficiently produces due to scarring or death of the native ependyma.

Figure 20:
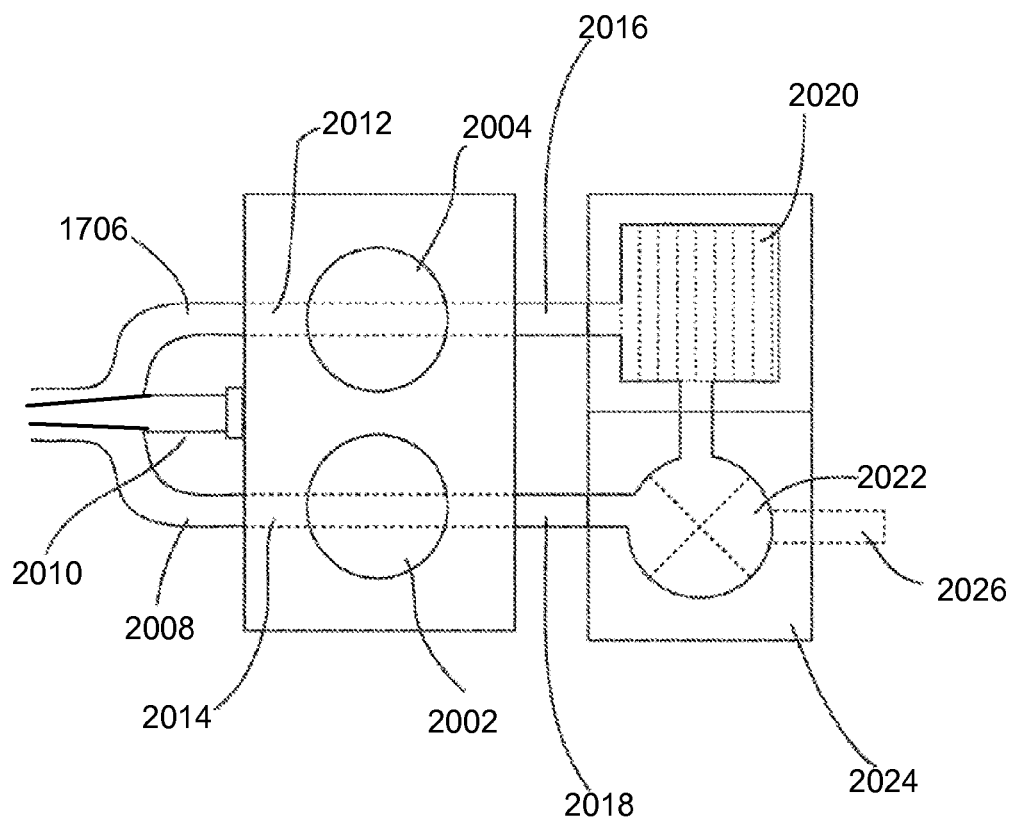
FIG. 20 illustrates an example filtration system for CSF, in accordance with some embodiments.

An example of such a filter is provided in relation to FIG. 20. In this example of a pumping system, a mechanical and/or chemical/antibody filter, or a replaceable cellular/biological cartridge comprised of ependyma on a 2D or 3D orientation is illustrated at 2020. Endogenous CSF would enter via the inlet 2014 from a source 2008 which can be a ventricular, cisternal or subarachnoid in origin or other body fluid. The fluid would be pumped in a bulk/pulsatile/oscillatory pattern by a pumping unit 2024 with bidirectional pumping mechanism 2022, the pumping cycle and flow which can be controlled by an embedded microprocessor which can take inputs from various detectors, including ECG or oximeter, and return information to the processing unit 2010 to control actuators and maintain homeostasis. Valves 2018 would on occasion allow the endogenous CSF to enter the filter 2020 and return to the system via outlet 2012 which is connected to other fluid conduits toward a ventricular, cisternal or subarachnoid location. The pumping system would be coordinated via a microprocessor to keep pressure/volume relationships within an acceptable range, as well as monitor and control impedance, including CSF outflow resistance and endogenous absorption and production of CSF. Additional filters and valves 2016 would prevent unwanted cell or cell products from returning to the CSF system. Reservoirs for accessing the pre-filtered CSF 2002 and post-filtered CSF 2004 can be available in some embodiments. The pumping and filtering system 2024 is modular, facilitating replacement of pump or filters. CSF may be stored if CSF volume is sufficient via a conduit 2026.

The novel CSF pathway may feature, in some embodiments, CSF flow to the patient only; in other embodiments, CSF from patient to system only for off-line processing, or, in yet other embodiments, real-time CSF in/flow coordinated by a control system monitoring pressure/volume (Compliance) and impedance of the native system. Cell sorting techniques including mechanical/chemical/antibody/energy (such as ultrasound) filters can be placed along the system to prevent certain or all cells from migrating from the bioreactor to the patient, thereby only allowing desirable fluid, cells and proteins/electrolytes to enter the native CSF. In some advanced embodiments utilizing a specialized ependymal and choroidal bioreactor, blood products could be inputted in order to output CSF.

Additionally, in some embodiments, these new bioreactor designs may be ideally suited for producing robust cells that are more capable for therapeutics, whether in brain or spinal repair, or other organ systems. For example, such a bioreactor could be modified to select for robust cells for heart repair, artificial pancreas, etc. (i.e., any cell or tissue or organ repair).

Figure 21:
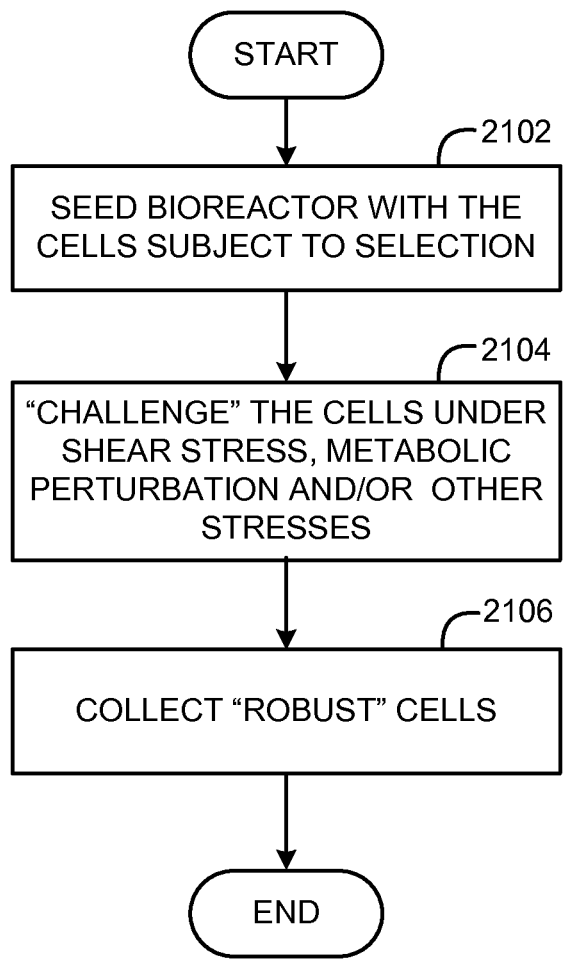
FIG. 21 is an example flow chart for the process of generating robust cells using an enhanced physiological mimicry bioreactor, in accordance with some embodiments.

FIG. 21 illustrates an example flowchart for the process of selecting for these "robust" cells. In this process, cells of interest may be seeded into a novel bioreactor (at 2102). These cells may include germ lines, tissues, organs, loose cells, etc. The cells are then "challenged" by the bioreactor (at 2104) through shearing, metabolic fluctuation and other stressors (such as temperature, alkalinity, osmolality, etc.). The cells those are still viable after the challenge may be the healthier and more robust cells. These cells may then be collected (at 2106) for downstream purposes. Often the challenged cells are not directly collected, but rather cells are collected after a maturation or selection stage.

In this manner, the problem of weak cells/tissue/organ is solved by subjecting ex vivo cells/tissue/organs to a bioreactor's environment (biomechanical shear stresses and metabolic environment, oxygenation, growth factors, etc.) before implantation in the body. An example for such a process used outside of the cerebrospinal space, includes applying a harsher bioreactor reproductive environment for in vitro/ex vivo fertilization procedures, where germ cells would face a tough environment before fertilization.

In sum, the present invention provides systems and methods for a medical device which enables an improvement over current cerebrospinal shunts, bioreactor designs, and therapies. Such systems and methods may include a multilayered tissue design whereby a matrix supports progenitor cells, and a luminal layer is further coated by an ependymal layer including tight junctions.

While this invention has been described in terms of several embodiments, there are alterations, modifications, permutations, and substitute equivalents, which fall within the scope of this invention. Although sub-section titles have been provided to aid in the description of the invention, these titles are merely illustrative and are not intended to limit the scope of the present invention.

It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

What is claimed is:

1. A biologically active medical device, wherein the biologically active medical device includes a lumen having a luminal surface and an abluminal surface, the biologically active medical device comprising:
   a matrix, wherein the matrix is capable of enabling cellular migration;
   a plurality of progenitor cells, wherein the progenitor cells are seeded on a luminal surface of the matrix; and
   a ciliated tissue located on the luminal surface of the matrix, wherein the ciliated tissue is located over the plurality of progenitor cells, and wherein the ciliated tissue is comprised of ependymal cells that express at least one of tight junctional complexes, zonula adherens, and gap junctions.

2. The biologically active medical device as recited in claim 1, wherein the progenitor cells include subpendymal progenitor cells.

3. The biologically active medical device as recited in claim 2, wherein the progenitor cells include stem cells.

4. The biologically active medical device as recited in claim 1, wherein the ciliated tissue is comprised of substantially at least one of choroid cells, tanacytes, and circumventricular organs.

5. The biologically active medical device as recited in claim 1, wherein the matrix includes imbedded cells.

6. The biologically active medical device as recited in claim 5, wherein the imbedded cells include any of glia, endothelial cells, and stem cells.

7. The biologically active medical device as recited in claim 1, wherein the matrix includes blood vessels.

8. The biologically active medical device as recited in claim 1, wherein the matrix is comprised of at least one of silicones, polyurethane, polyethylene, polypropylene, polyvinyl chloride, agarose gel, collagen, elastin, capillary networks include fibronectin and endothelial cells.

9. The biologically active medical device as recited in claim 1, further comprising a microfluidic circuit coupled to the abluminal surface of the matrix.

10. The biologically active medical device as recited in claim 9, wherein the biologically active medical device is incorporated into an anthropomorphic bioreactor.

11. The biologically active medical device as recited in claim 1, wherein the biologically active medical device is oriented into a tubular structure in order to form a cerebrospinal shunt.

* * * * *